United States Patent [19]

Musser et al.

[11] Patent Number: 5,229,516

[45] Date of Patent: Jul. 20, 1993

[54] SUBSTITUTED INDOLE-, INDENE-, PYRANOINDOLE- AND TETRAHYDROCARBAZOLE-ALKANOIC ACID DERIVATIVES AS INHIBITORS OF PLA2 AND LIPOXYGENASE

[75] Inventors: John H. Musser, Alameda, Calif.; Anthony F. Kreft, III, Langhorne, Pa.; Amedeo A. Failli, Princeton Junction, N.J.; Christopher A. Demerson, Kirkland, Canada; Uresh S. Shah, Plainsboro, N.J.; James A. Nelson, Washington Crossing, Pa.

[73] Assignee: American Home Products Corporation, New York, N.Y.

[21] Appl. No.: 911,434

[22] Filed: Jul. 10, 1992

Related U.S. Application Data

[63] Continuation-in-part of Ser. No. 596,134, Oct. 11, 1990, abandoned, which is a continuation-in-part of Ser. No. 428,260, Oct. 27, 1989, abandoned.

[51] Int. Cl.$^5$ .................. C07D 215/14; C07D 401/12; C07D 405/14
[52] U.S. Cl. .................... 546/172; 546/152; 546/174; 546/175; 546/176; 546/180
[58] Field of Search ............... 546/172, 152, 174, 175, 546/176, 180

[56] References Cited

U.S. PATENT DOCUMENTS

| | | | |
|---|---|---|---|
| 3,654,349 | 4/1972 | Shen et al. | 260/515 |
| 3,896,145 | 7/1975 | Berger et al. | 260/315 |
| 3,939,178 | 2/1976 | Demerson et al. | 260/326.28 |
| 4,057,559 | 11/1977 | Asselin et al. | 260/315 |
| 5,095,031 | 3/1992 | Brooks et al. | 514/415 |
| 5,157,122 | 10/1992 | Hughes et al. | 546/176 |

FOREIGN PATENT DOCUMENTS 0275667 7/1988 European Pat. Off. .

*Primary Examiner*—C. Warren Ivy
*Assistant Examiner*—James H. Turnipseed
*Attorney, Agent, or Firm*—George Tarnowski

[57] ABSTRACT

There are disclosed compounds of the formula $A(CH_2)_nO\text{-}B$ wherein

A is $C_4$–$C_8$ alkyl, phenoxyethyl, phenoxyphenyl or a group having the formula

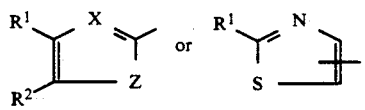

wherein X is $-\underset{\underset{R^3}{|}}{N}-$ or $-\underset{\underset{R^3}{|}}{C}-$;

Z is $-\underset{\underset{R^3}{|}}{C}=\underset{\underset{R^3}{|}}{C}-$, $-\underset{\underset{R^3}{|}}{C}=N-$, $-N=\underset{\underset{R^3}{|}}{C}-$, $-\underset{\underset{R^3}{|}}{N}-$, $-S-$ or $-O-$;

$R^1$ is hydrogen, lower alkyl, phenyl or phenyl substituted with trifluoromethyl;
$R^2$ is hydrogen or lower alkyl; or
$R^1$ and $R^2$ taken together form a benzene ring;
$R^3$ is hydrogen or lower alkyl;
n is 1–2;
B is

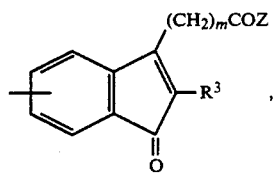

(Abstract continued on next page.)

-continued

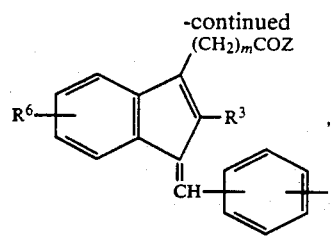

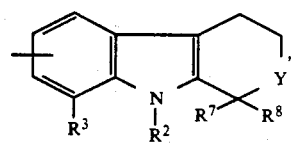

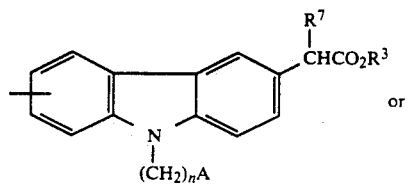

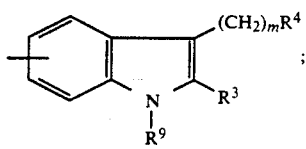

wherein

R$^4$ is —CO$_2$R$^2$, —N(OH)$\overset{O}{\overset{\|}{C}}$NH$_2$, —N(OH)$\overset{O}{\overset{\|}{C}}$R$^7$, —NH$\overset{O}{\overset{\|}{C}}$NHOH, —C$\overset{O}{\overset{\|}{N}}$(OH)R$^7$ or —C$\overset{O}{\overset{\|}{N}}$HSO$_2$R$^{11}$;

m is 0-3;
R$^5$ is

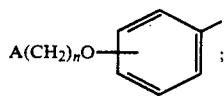

or phenyl or phenyl substituted by halo, lower alkylthio, lower alkylsulfinyl or lower alkylsulfonyl;

R$^6$ is A(CH$_2$)$_n$O— or halo; with the proviso that when R$^6$ is halo, R$^5$ is

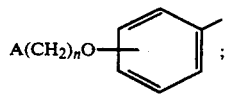

R$^7$ is lower alkyl;
Y is —CH$_2$— or —O—;
R$^8$ is lower alkyl or —(CH$_2$)$_m$CO$_2$R$^3$;
R$^9$ is $-\overset{O}{\overset{\|}{C}}R^{10}$ or —CH$_2$R$^{10}$;
R$^{10}$ is lower alkyl, phenyl, phenyl substituted with carboxy, halo, loweralkylthio or loweralkylsulfinyl, pyridyl, furanyl or quinolinyl;
R$^{11}$ is lower alkyl or phenyl;
Z is hydrogen, lower alkyl or —N(CH$_3$)OH;

and the pharmacologically acceptable salts thereof, and their use in the treatment of inflammatory conditions, such as rheumatoid arthritis, ulcerative colitis, psoriasis and other immediate hypersensitivity reactions; in the treatment of leukotriene-mediated naso-bronchial obstructive air-passageway conditions, such as allergic rhinitis, allergic bronchial asthma and the like; and as gastric cytoprotective agents.

29 Claims, No Drawings

SUBSTITUTED INDOLE-, INDENE-, PYRANOINDOLE- AND TETRAHYDROCARBAZOLE-ALKANOIC ACID DERIVATIVES AS INHIBITORS OF PLA2 AND LIPOXYGENASE

This is a continuation-in-part of U.S. Ser. No. 07/596,134, filed Oct. 11, 1990, now abandoned which is a continuation-in-part of U.S. Ser. No. 07/428,260, filed Oct. 27, 1989, and now abandoned.

This invention relates to novel substituted indene-, indole-, pyranoindole- and tetrahydrocarbazole alkanoic acid derivatives possessing lipoxygenase inhibitory, phospholipase $A_2$ inhibitory and leukotriene antagonist activity, which are useful as anti-inflammatory, antiallergic and cytoprotective agents.

It is now well-established that arachidonic acid (AA) is metabolized in mammals by two distinct pathways. The metabolism of arachidonic acid by cyclooxygenase enzymes results in the production of prostaglandins and thromboxanes. The physiological activity of the prostaglandins has already been amply elucidated in recent years. It is now known that prostaglandins arise from the endoperoxides $PGG_2$ and $PGH_2$ by the cyclooxygenase pathway of arachidonic acid metabolism. These endoperoxides are also the precursors of the thromboxanes (Tx) $A_2$ and $B_2$. $TxA_2$ is a vasoconstrictor which stimulates platelet aggregation. In the normal situation, the vasoconstrictive and platelet aggregating properties of the thromboxanes are balanced by another product arising from the endoperoxides in the cyclooxygenase pathway, prostacyclin ($PGI_2$), which is a vasodilator with platelet aggregation inhibitory activity. In the event prostacyclin synthesis is impaired and/or platelet activation is enhanced, then thrombosis and vasoconstriction is favored. The role of prostanoids in haemostatis and thrombosis are reviewed by R. J. Gryglewski, *CRC Crit. Rev. Biochem.*, 291 (1980) and J. B. Smith, *Am. J. Pathol.*, 99, 743 (1980). Cyclooxygenase metabolites are known to participate directly in the inflammatory response [see Higgs et al., Annals of Clinical Research, 16, 287-299 (1984)]. This is through their vasodepressor activities, participation in pain and fever augmentation of peptide mediator vascular permeability and edema forming properties. Finally, various aspects of cell mediated immunity are influenced by cyclooxygenase products.

The other pathway of AA metabolism involves lipoxygenase enzymes and results in the production of a number of oxidative products called leukotrienes. The latter are designated by the LT nomenclature system, and the most significant products of the lipoxygenase metabolic pathway are the leukotrienes $B_4$, $C_4$ and $D_4$. The substance denominated slow-reacting substance of anaphylaxis (SRS-A) has been shown to consist of a mixture of leukotrienes, with $LTC_4$ and $LTD_4$ as the primary products and having varying amounts of other leukotriene metabolites [see Bach et al., *J. Immun.*, 215, 115-118 (1980); *Biochem. Biophys. Res. Commun.*, 93, 1121-1126 (1980)].

The significance of these leukotrienes is that a great deal of evidence has been accumulated showing that leukotrienes participate in inflammatory reactions, exhibit chemotactic activities, stimulate lysosomal enzyme release and act as important factors in the immediate hypersensitivity reaction. It has been shown that $LTC_4$ and $LTD_4$ are potent bronchoconstrictors of the human bronchi [see Dahlen et al., *Nature*, 288, 484-486 (1980) and Piper, *Int. Arch. Immunol.*, 76, suppl. 1, 43 (1985)] which stimulate the release of mucus from airways in vitro [Marom et al., *Am. Rev. Resp. Dis.*, 126, 449 (1982)], are potent vasodilators in skin ]see Bisgaard et al., *Prostaglandins*, 23, 797 (1982)], and produce a wheal and flare response [Camp et al., *Br. J. Pharmacol.*, 80, 497 (1983)]. The nonpeptide leukotriene, $LTB_4$, is a powerful chemotactic factor for leukocytes [see A. W. Ford-Hutchinson, *J. Roy. Soc. Med.*, 74, 831-833 (1981), which stimulates cell accumulation and affects vascular smooth muscle [see Bray, *Br. Med. Bull.*, 39, 249 (1983)]. The activity of leukotrienes as mediators of inflammation and hypersensitivity is extensively reviewed in Bailey and Casey, *Ann. Reports Med. Chem.*, 19, 87 (1986).

Phospholipase $A_2$ ($PLA_2$) is the critical rate limiting enzyme in the arachidonic acid (AA) cascade since it is responsible for the hydrolysis of esterified AA from the C-2 position of membrane phospholipids. This reaction generates two products (1) free AA which is then available for subsequent metabolism by either the cyclooxygenase or lipoxygenase enzymes and (2) lysophospholipid. When alkylarachidonoyl-glycerophosphatidylcholine is acted upon by the $PLA_2$ the generation of platelet activating factor (PAF) is initiated; PAF is pro-inflammatory in its own right [see Wedmore et al., *Br. J. Pharmacol.*, 74, 916-917 (1981)]. In this regard it may be noted that the anti-inflammatory steroids are thought to inhibit eicosanoid synthesis by inducing the synthesis of a $PLA_2$ inhibitory protein denominated macrocortin or lipomodulin [see Flower et al, *Nature*, London, 278, 456 (1979) and Hirata et al., *Proc. Natn. Acad. Sci. U.S.A.*, 77, 2533 (1980)].

As the initial step leading to subsequent conversion of AA to the various eicosanoids by the cyclooxygenase and lipoxygenase pathways, the $PLA_2$-mediated release of AA from membrane phospholipids is a critical event in attempting to deal with the various physiological manifestations which are based on the activity of the eicosanoids and/or PAF. Thus, while $PLA_2$ has been shown to be required for platelet aggregation [Pickett et al., *Biochem. J.*, 160, 405 (1976)], cardiac contraction and excitation [Geisler et al., *Pharm. Res. Commun.*, 9, 117 (1977)], as well as prostaglandin synthesis ]Vogt, *Adv. Prostagl. Thromb.* 3, 89 (1978)], the inhibition of $PLA_2$ is indicated in the therapeutic treatment of both PAF induced or cyclooxygenase and/or lipoxygenase pathway product-mediated physiological conditions.

There is also evidence that products of the cyclooxygenase/lipoxygenase pathways play key roles in both the pathogenesis of gastric mucosal damage due to extracellular (gastric and intestinal contents, microorganisms, and the like) or intracellular (ischemia, viruses, etc.) agents, as well as in cytoprotection against such damage. Thus, on the one hand prostaglandins exert a cytoprotective effect on the gastric mucosa [see Robert, *Gastroenterology*, 77, 761-767 (1979)] and this action of the prostaglandins, especially of the E series, is considered to be of importance in the treatment of gastrointestinal ulceration [see Isselbacher, *Drugs*, 33 (suppl.), 38-46 (1987)]. On the other hand, ex vivo experiments have shown that gastric mucosal tissue from ethanol-pretreated rats is capable of $LTC_4$ generation and that this $LTC_4$ production is quantitatively related to the severity of the ethanol damage [see Lange et al., *Naunyn-Schmiedeberg's Arch. Pharmacol. Suppl.*, 330, R27, (1985)]. It has also been demonstrated that $LTC_4$ can induce vasoconstriction in both venous and arteriolar vessels in the rat submucosa [see Whittle, *IUPHAR Ninth Int. Cong. of Pharm.* S30-2, London, England (1984)]. This is significant since ethanol-induced lesion formation in gastric mucosa may be multifactorial with, for example, stasis of gastric blood flow contributing significantly to the development of the hemorrhagic necrotic aspects of the tissue injury [see Guth et al., *Gastroenterology*, 87, 1083-90 (1984)]. Moreover, in the anesthetized cat, exogenous $LTD_4$ evokes both increased pepsin secretion and decreased transgastric potential [Pendleton et al., *Eur J. Pharmacol.*, 125, 297-99 (1986)]. A particularly significant recent finding in this regard is that 5-lipoxygenase inhibitors and some leukotriene antagonists protect the gastric mucosa against lesions induced by the oral or parenteral administration of most nonsteroidal anti-inflammatory drugs ]see Rainsford, *Agents and Actions*, 21, 316-319 (1987)]. Platelet activating factor (PAF) is also implicated as a mediator of gastrointestinal damage, and it has been recently shown that 5-lipoxygenase inhibitors inhibit PAF-induced gastric mucosal damage (*Gastroenterology*, 96, A55, A434, 1989). Accordingly, a significant body of evidence implicates the involvement of lipoxygenase products in the development of pathological features associated with gastric mucosal lesions, such as for example, those induced by ethanol exposure and administration of non-steroidal anti-inflammatory drugs. Thus, compounds which inhibit the biological effects of leukotrienes and PAF and/or which control the biosynthesis of these substances, as by inhibiting 5-lipoxygenase, are considered to be of value as cytoprotective agents.

Accordingly, the biological activity of the leukotrienes and SRS's, and of lipoxygenase as the enzyme leading to the metabolism of AA to leukotrienes, indicates that a rational approach to drug therapy to prevent, remove or ameliorate the symptoms of allergies, anaphylaxis, asthma and inflammation and for gastric cytoprotection must focus on either blocking the release of mediators of these conditions or antagonizing their effects. Thus, compounds which inhibit the biological effects of the leukotrienes and SRS's and/or which control the biosynthesis of these substances, as by inhibiting the $PLA_2$-mediated release of arachidonic acid from membrane phospholipids, or by inhibiting lipoxygenase, are considered to be of value in treating such conditions as allergic bronchial asthma, allergic rhinitis, as well as in other immediate hypersensitivity reactions and in providing gastric cytoprotection.

It has now been found that certain novel substituted indene-, indole-, pyranoindole- and tetrahydrocarbazole alkanoic acid derivatives inhibit $PLA_2$ and lipoxygenase, and antagonize products of the lipoxygenase pathway, and so are useful as anti-inflammatory, anti-allergic and cytoprotective agents. The present invention provides novel compounds having the following formula:

$$A(CH_2)_nO—B$$

wherein

A is $C_1$-$C_8$ alkyl, phenoxyethyl, phenoxyphenyl or a group having the formula

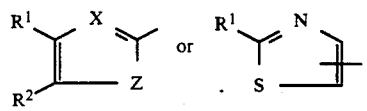

wherein

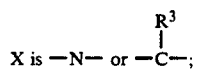

X is —N— or —C—;

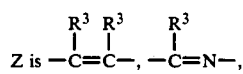

Z is $-C=C-$, $-C=N-$,

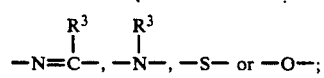

$-N=C-$, $-N-$, $-S-$ or $-O-$;

$R^1$ is hydrogen, lower alkyl, phenyl or phenyl substituted with trifluoromethyl;
$R^2$ is hydrogen or lower alkyl; or
$R^1$ and $R^2$ taken together form a benzene ring;
$R^3$ is hydrogen or lower alkyl;
n is 1-2;
B is

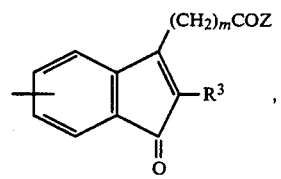

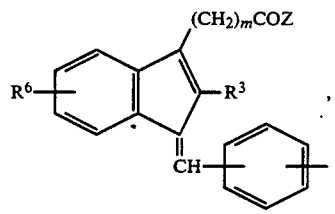

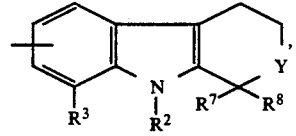

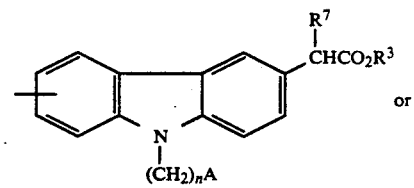

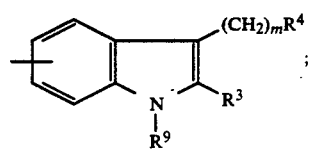

wherein $R^4$ is $-CO_2R^2$, $-N(OH)\overset{O}{\overset{\|}{C}}NH_2$, $-N(OH)\overset{O}{\overset{\|}{C}}R^7$, $-NH\overset{O}{\overset{\|}{C}}NHOH$, $-\overset{O}{\overset{\|}{C}}N(OH)R^7$ or $-\overset{O}{\overset{\|}{C}}NHSO_2R^{11}$;

m is 0–3;
$R^5$ is

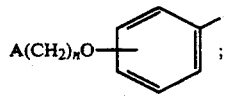

or phenyl or phenyl substituted by halo, lower alkylthio, lower alkylsulfinyl or lower alkylsulfonyl;

$R^6$ is $A(CH_2)_nO-$ or halo; with the proviso that when $R^6$ is halo, $R^5$ is

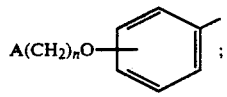

$R^7$ is lower alkyl;
Y is $-CH_2-$ or $-O-$;
$R^8$ is lower alkyl or $-(CH_2)_mCO_2R^3$;

$R^9$ is $-\overset{O}{\overset{\|}{C}}R^{10}$ or $-CH_2R^{10}$;

$R^{10}$ is lower alkyl, phenyl, phenyl substituted with carboxy, halo, loweralkylthio or loweralkylsulfinyl, pyridyl, furanyl or quinolinyl;
$R^{11}$ is lower alkyl or phenyl;
Z is hydrogen, lower alkyl or $-N(CH_3)OH$;
and the pharmacologically acceptable salts thereof.

The terms "lower alkyl" and "lower alkoxy" refer to moieties having 1–6 carbon atoms in the carbon chain. The term "halo" refers to fluoro, chloro or bromo.

The grouping A embraces, inter alia, 5- or 6- membered unsaturated nitrogen, sulfur or oxygen containing mono- or benzofused-heterocycles, optionally substituted with lower alkyl or phenyl. The foregoing definition embraces the following heterocyclic moieties: furyl, pyrrolyl, thienyl, oxazolyl, thiazolyl, imidazolyl, pyridyl, pyrazinyl, pyrimidinyl, benzofuranyl, benzothienyl, benzothiazolyl, indolyl, benzoxazolyl, quinolinyl, quinazolinyl, benzimidazolyl, quinoxalinyl, quinazolinyl and the like. Especially preferred are quinolinyl, benzothiazolyl, benzimidazolyl and 2-phenylthiazole.

The compounds of the invention can form pharmacologically acceptable salts from pharmacologically acceptable organic and inorganic acids such as hydrochloric, hydrobromic, sulfonic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, itaconic and benzenesulfonic. The compounds which are carboxylic acids are capable of forming alkali metal and alkaline earth carboxylates and carboxylates of pharmacologically acceptable cations derived from ammonia or a basic amine. Examples of the latter include but are not limited to cations such as ammonium, mono-, di-, and trimethylammonium, mono-, di- and triethylammonium, mono-, di-, and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butyl-piperidinium, 2-methylpiperidinium, 1-ethyl-2-methylpiperidinium, mono-, di- and triethanolammonium, ethyl diethanolammonium, n-butylmonoethanolammonium, tris(hydroxymethyl)methylammonium, phenylmonoethanolammonium, and the like.

The compounds of the invention can be prepared by the following reaction schemes. When it is desired to prepare compounds having the formula

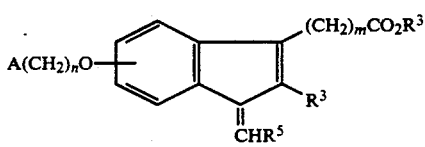

p-methoxybenzaldehyde, for example, is reacted with propionic anhydride, followed by reduction and ring closure to yield the intermediate 6-methoxy-2-methyl-1-indanone

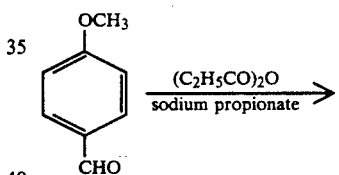

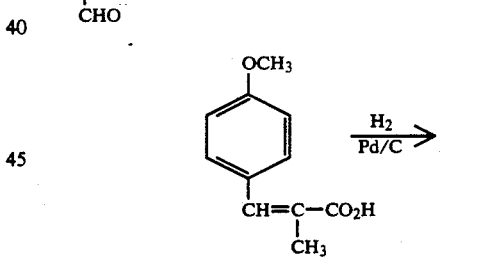

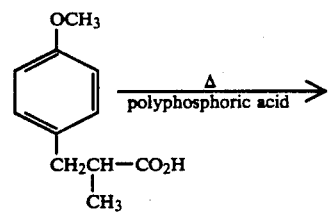

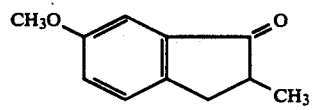

The indanone intermediate is then subjected to demethylation and the resulting hydroxyindanone is reacted with an appropriate haloalkyl-A compound where A is as defined hereinbefore and hal is halo

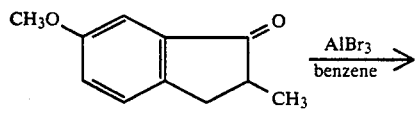

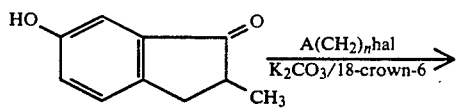

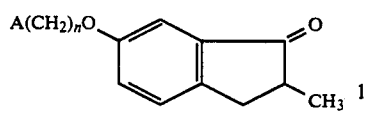

The latter intermediate, where n=1, is reacted with triethylphosphonoacetate in sodium hydride to yield an intermediate indene-3-acetic acid ethyl ester, which is then hydrolyzed and concomitantly reacted with an appropriate reactant to introduce the desired $R^5$-methylene group onto the indene-3-acetic acid moiety, exemplified below by the introduction of a p-chlorophenylmethylene grouping

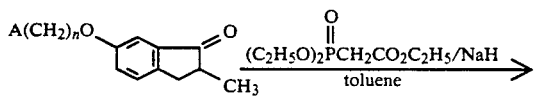

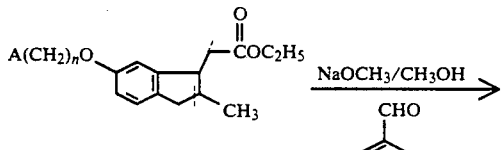

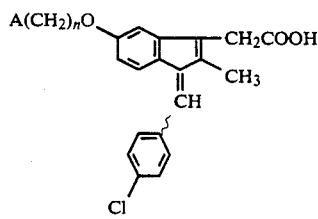

Compounds in which the $R^5$ group is lower alkylthiophenyl can be prepared by using an appropriate loweralkylthiobenzaldehyde. The compounds in which $R^5$ is a loweralkylsulfinylphenyl grouping can be prepared from the loweralkylthiophenyl-containing compounds by reaction with 30% $H_2O_2$ in chloroform/acetic acid.

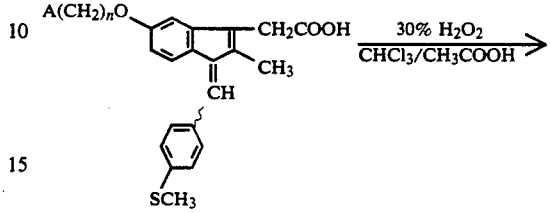

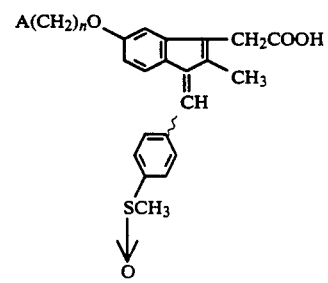

In an alternative preparation scheme, the intermediate hydroxyindanone can be reacted with cyanoacetic acid to give the corresponding hydroxyindene-3-acetic acid, which is then esterified before introduction of the $R^5$-methylene grouping in order to facilitate the purification of desired intermediates. Since introduction of the $R^5$-methylene grouping is accompanied by ester hydrolysis, the intermediate free acid is re-esterified to facilitate purification followed by reaction with an appropriate haloalkyl-A group to yield the desired final product

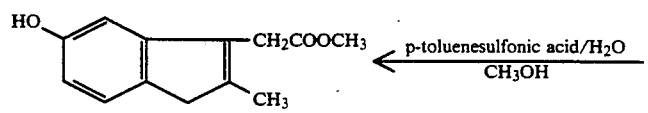

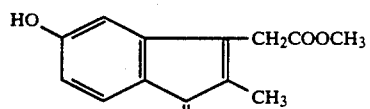
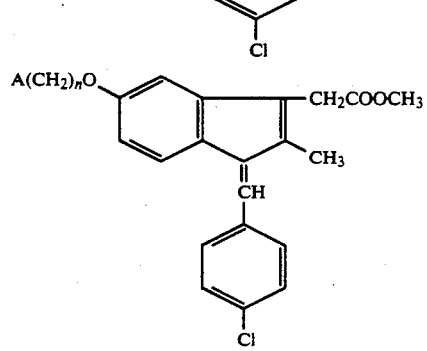
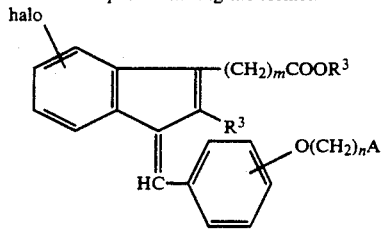
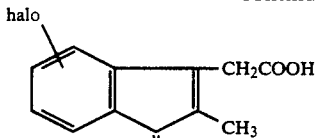

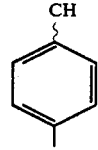

can be prepared by reacting a halo-indene-3-acetic acid with a A(CH$_2$)$_n$-containing benzaldehyde prepared from the corresponding individual components

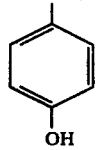

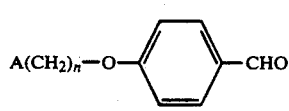

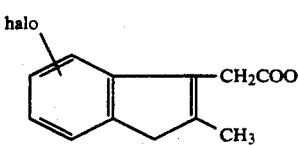

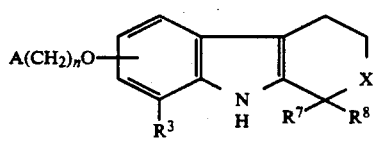

In all of the above-outlined reaction schemes, the final product free acids can be esterified via conventional methods and in like fashion, final product esters can be hydrolyzed by known procedures to yield the corresponding free acids.

Compounds of the invention having the formula in which X is —CH$_2$— can be prepared by initially reacting 4-methoxyphenylhydrazine with, for example, 2-carbomethoxymethyl-2-alkylcyclohexanone, followed by ring closure to yield an intermediate tetrahydro-methoxy-1H-carbazole-1-acetic acid

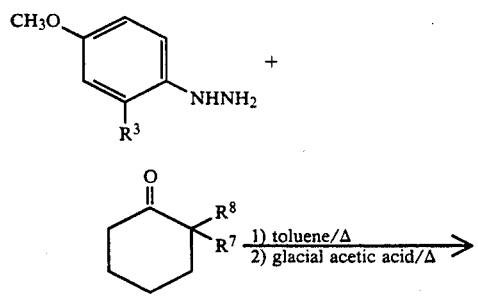

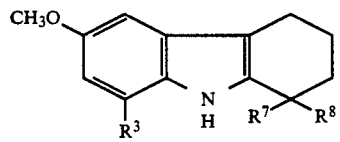

The latter intermediate is demethylated with hydrobromic acid to yield the corresponding hydroxy compound, which is then reacted with an appropriate halo-loweralkyl-A compound by one of several routes. In one such preparative sequence, two equivalents of the starting material, A(CH$_2$)$_n$hal, are reacted with a metal derivative of the hydroxycarbazole-1-acetic acid to form an intermediate ester ether which is hydrolyzed to yield the desired final products. The metal derivative of the hydroxycarbazole-1-acetic acid may be prepared by treating the acid with an alkali metal alkoxide, such as sodium methoxide.

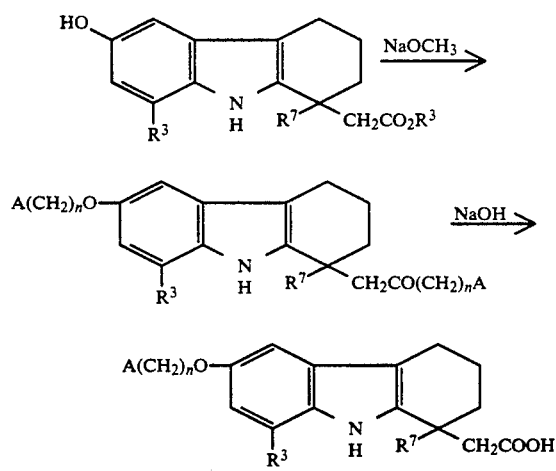

In the above sequence, A, n, m and R$^7$ are as defined hereinbefore and hal denotes chloro, bromo or iodo.

In an alternative sequence, it is possible to use only one equivalent of starting material A(CH$_2$)$_n$hal with the metal derivative to obtain the desired final product directly, without proceeding through the ethyl ester intermediate.

In yet another reaction sequence, the desired final products can be prepared by the alkylation of alkyl esters of the hydroxycarbazole-1-acetic acid:

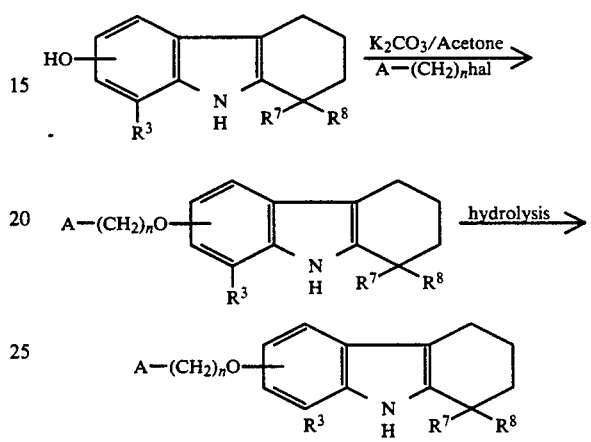

where A, n, m, R$^3$, R$^7$, R$^8$ and hal are as defined hereinbefore. Hydrolysis is carried out using a dilute hydroxide, such as for example sodium hydroxide.

Compounds of the invention having the formula

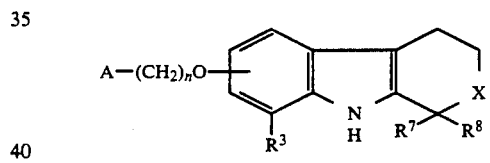

in which X is —O— can be prepared by the above-outlined reaction sequences which differ only in the preparation of the starting tetrahydro-6-hydroxypyrano[3,4-b]indole-1-lower alkanoic acid esters. The latter can be prepared by the reaction of, for example, a 5-benzyloxytryptophol with a loweralkyl-(R$^7$-carbonyl)lower alkanoate in boron trifluoride etherate to yield an intermediate 1-R$^7$-tetrahydro-6-(phenylmethoxy)pyrano-[3,4-b]indole-1-alkanoic acid ester, which is then subjected to reduction to yield the corresponding 6-hydroxy ester

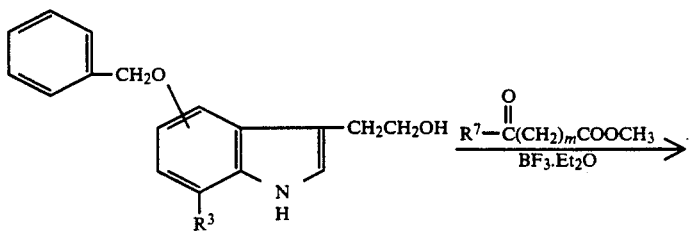

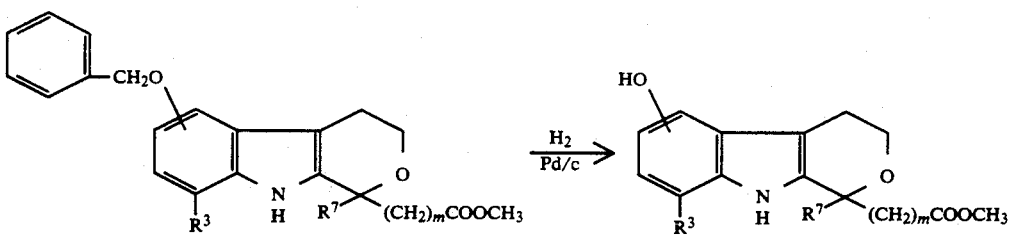

The latter intermediate can then be reacted as outlined earlier with an appropriate $A(CH_2)_n$hal compound to yield the desired final compounds.

Another scheme by which the starting tetrahydro-6-hydroxypyrano[3,4-b]indole 1-alkanoic acid ester can be prepared involves reducing 7-loweralkyltryptophol to 7-loweralkyl-2,3-dihydrotryptophol, followed by reacting the latter with potassium nitrosodisulfonate to yield a 7-loweralkyl-5-hydroxytryptophol, which is then reacted with a suitable lower alkyl-3-methoxy-lower alkanoate to yield the desired intermediate tetrahydro-6-hydroxypyrano[3,4-b]indole-1-loweralkanoic acid ester

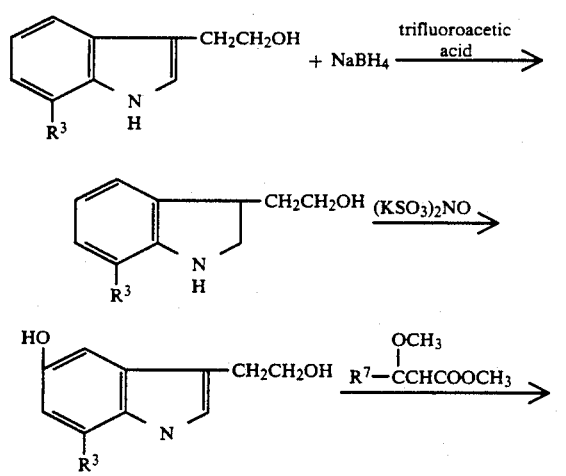

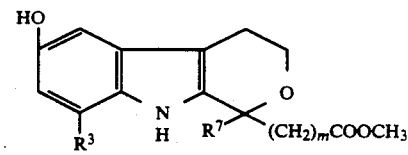

As with the previously described indene-1-acetic acid derivatives, the carbazole final product free acids can be esterified via conventional methods and in like fashion, final product esters can be hydrolyzed by known procedures to yield the corresponding free acids.

Compounds of the invention having, for example, the formula

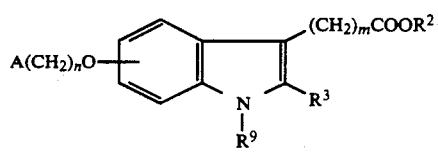

can be prepared by reacting 5-hydroxy-2-methyl-1H-indole-3-loweralkanoic acid with an appropriate $A(CH_2)_n$hal compound in the presence of sodium methoxide/methanol to yield the intermediate $A(CH_2)_n$O-containing indole alkanoic acid derivative, which is then esterified and reacted with a suitable substituted benzyl or benzoyl halide to yield the desired final product in ester form, which can be converted to the free acid form by conventional methods.

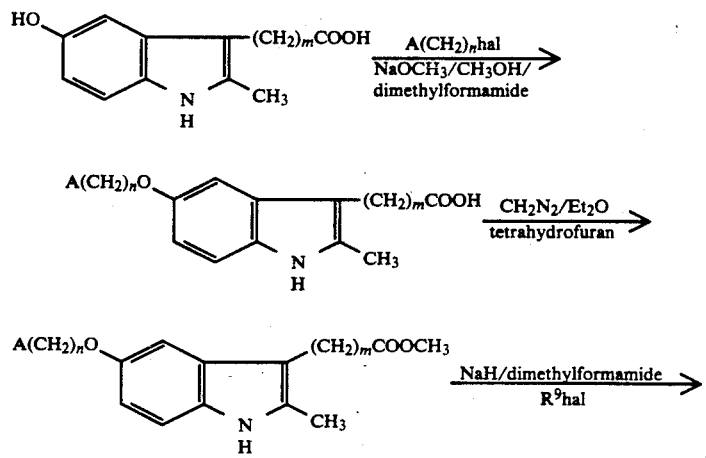

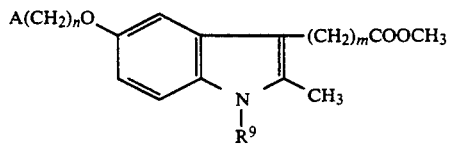

Compounds of the invention having the formula

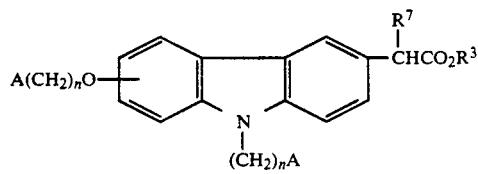

can be prepared via the following reaction sequence: 4-benzyloxyaniline is reacted with sodium nitrite in the presence of stannous chloride to yield 4-benzyloxyhydrazine, which is reacted with α-methyl-3-oxocyclohexanone acetic acid to yield an intermediate α-methyl-tetrahydrocarbazole acetic acid, which is esterified with ethanol to yield the intermediate ethyl ester.

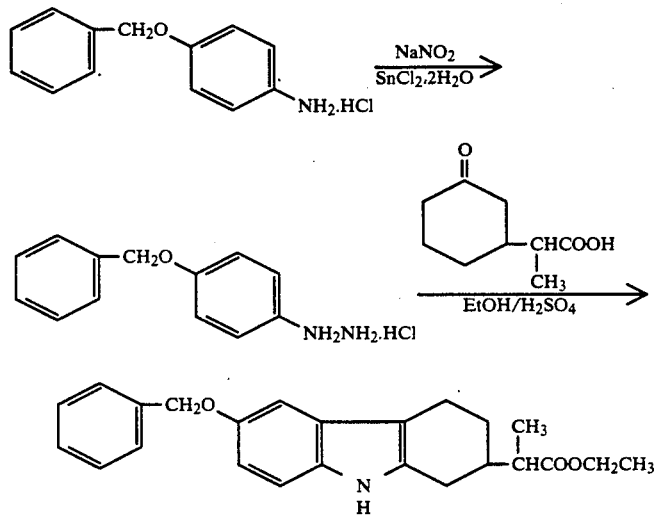

The α-methyl tetrahydrocarbazole acetic acid ester intermediate is reacted under reflux with chloranil in xylene under a nitrogen atmosphere to yield the corresponding α-methylcarbazole acetic acid, which is reduced by hydrogenation to remove the benzyloxy group, yielding the 6-hydroxy-α-methyl carbazole acetic acid ester intermediate.

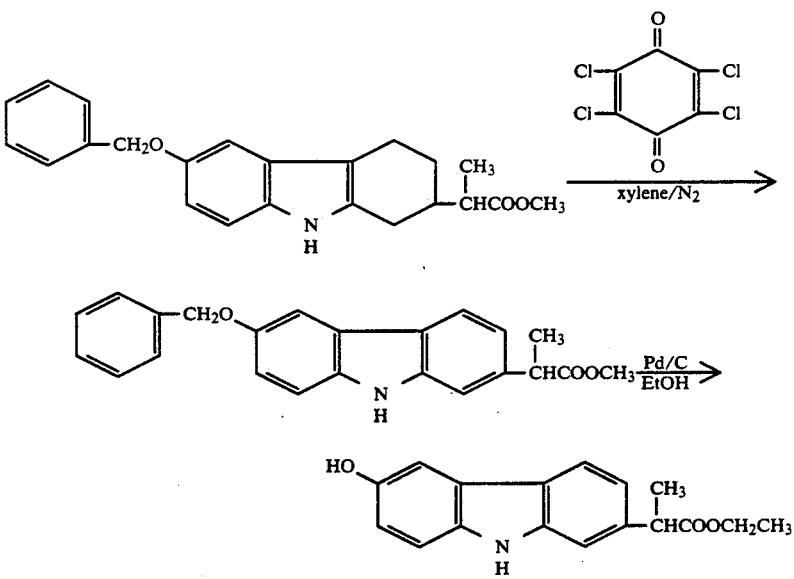

The latter intermediate is then hydrolyzed to give the free carboxylic acid intermediate, which is then reacted with an appropriate haloalkyl-A compound, where A is as hereinbefore defined and hal is halo, to yield the desired final product.

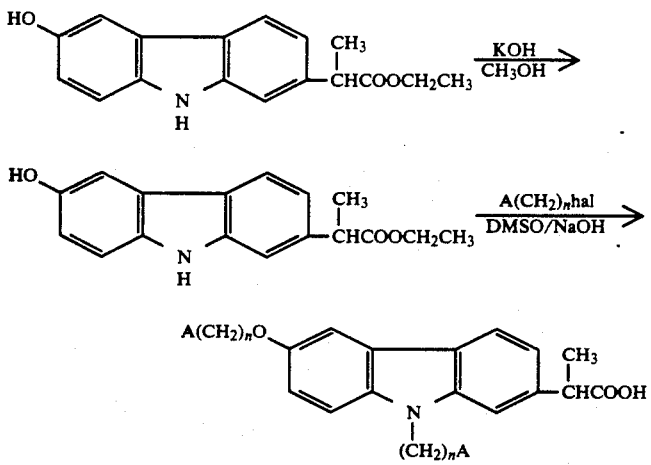

The conventional starting materials used in the reaction sequences outlined above are available commercially or can be prepared by methods known in the art. Thus, for example, the intermediate compound 2-bromomethylquinoline can be prepared by the following reaction sequence:

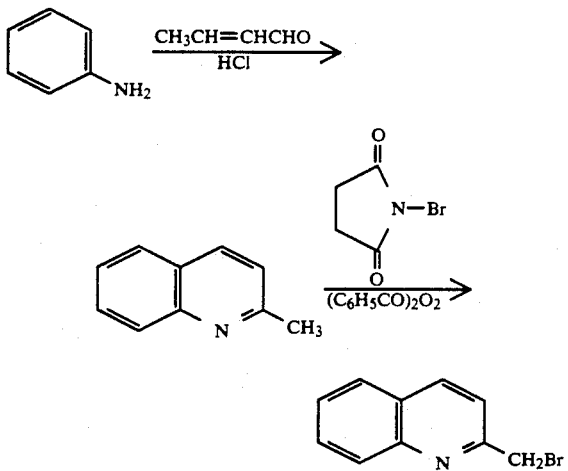

The benzo-fused heterocyclic compounds used in the above reaction sequences are also either commercially available or can be prepared by methods conventional in the art. Thus, for example, such intermediates as 1-methyl-2-chloromethylbenzimidazole, 2-chloromethylbenzthiazole and 2-chloromethylbenzoxazole can be prepared by the following reaction scheme

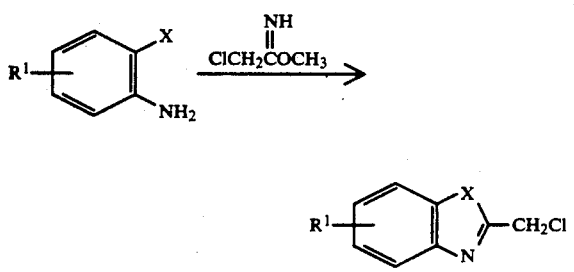

wherein X is O, S or $NCH_3$. The reaction is preferably carried out at a controlled low temperature in an organic solvent, such as methylene chloride.

Certain compounds within the scope of the invention exist in the form of E and Z stereoisomers and the individual isomers can be differentiated by the prefixes E and Z, as assigned by the accepted sequence rules procedures. Accordingly, the present invention embraces the E, Z and mixed isomer forms of those final product compounds exhibiting this form of stereoisomerism.

The compounds of the invention, by virtue of their ability to inhibit the activity of $PLA_2$ enzyme, as well as that of lipoxygenase enzyme and to antagonize mediators arising from the enzymatic pathway, are useful in the treatment of conditions mediated by products of the oxidation of arachidonic acid. Accordingly, the compounds are indicated in the treatment of such diseases as rheumatoid arthritis, inflammatory bowel disease, osteoarthritis, tendinitis, bursitis, psoriasis (and related skin inflammation) and similar conditions involving inflammation. Moreover, by virtue of their ability to antagonize the effect of $LTC_4$, $LTD_4$ and $LTE_4$, which are the constituents of SRS-A, they are useful for the inhibition of symptoms induced by these leukotrienes. Accordingly, the compounds are indicated in the prevention and treatment of those disease states in which $LTC_4$, $LTD_4$ and $LTE_4$ are causative factors, for example allergic rhinitis, allergic bronchial asthma and other leukotriene mediated nasobronchial obstructive air-passageway conditions, as well as in other immediate hypersensitivity reactions, such as allergic conjunctivitis. The compounds are especially valuable in the prevention and treatment of allergic bronchial asthma.

The compounds of the invention are cytoprotective agents and are considered especially useful when administered with conventional non-steroidal anti-inflammatory drugs, whose major side effect is gastrointestinal irritation. The cytoprotective effect of the compounds of the invention significantly reduces the gastroirritant impact of conventional anti-inflammatory drugs. This effect is based not only on the ability of the compounds of the invention to inhibit the biological effects of leukotrienes and/or control the biosynthesis of these substances, as by inhibiting lipoxygenase, but also by a shunting effect, whereby the control of the lipoxygenase pathway "shunts" the oxidation of arachidonic acid into the cyclooxygenase pathway, giving rise to an increase in the formation of cytoprotective prostaglandins. These biological effects make the compounds of the invention especially useful in treating such conditions as erosive esophagitis, inflammatory bowel disease and induced hemorrhagic lesions such as those induced by alcohol or non-steroidal anti-inflammatory drugs (NSAID's), hepatic ischemia, noxious agent induced damage or necrosis of hepatic, pancreatic, renal or myocardial tissue; liver parenchymal damage caused by hepatotoxic agents such as carbon tetrachloride and D-galactosamine; ischemic renal failure; disease-induced hepatic damage; bile salt-induced pancreatic or gastric damage; trauma or stress-induced cell damage; and glycerol-induced renal failure.

When the compounds of the invention are employed in the treatment of allergic airway disorders, as anti-inflammatory agents and/or as cytoprotective agents, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethyl-cellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic. For administration by inhalation or insufflation, the compounds may be formulated into an aqueous or partially aqueous solution, which can then be utilized in the form of an aerosol.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day.

The PLA$_2$ and lipoxygenase inhibitory and leukotriene antagonist effects, as well as the anti-inflammatory and potential gastroirritant effects of the compounds of the invention, may be demonstrated by standard pharmacological procedures which are described more full in the examples given hereinafter.

These procedures, inter alia, determine the specificity of action of the compounds of the invention as PLA$_2$ inhibitors as measured by their ability to inhibit the synthesis of LTB$_4$ and PGE$_2$ by rat glycogen-elicited polymorphonuclear leukocytes, as well as measure their ability to inhibit arachidonic acid release mediated by human and non-human source PLA$_2$. The procedures further measure the ability of the compounds of the invention to inhibit, in vivo, the activity of exogenously administered PLA$_2$. The pharmacological testing additionally demonstrates the ability of the compounds of the invention to inhibit, in vivo, the lipoxygenase and cyclooxygenase pathways of arachidonic acid metabolism; the in vitro and in vivo leukotriene antagonist activity of the compounds of the invention; and also measures the in vivo activity of the compounds as anti-inflammatory agents in the rat carrageenan paw edema assay. Finally, the potential of the compounds to induce acute gastroirritation in rats is measured in a test procedure.

The following examples show the preparation and pharmacological testing of compounds within the invention.

EXAMPLE 1

3-[(4-Chlorophenyl)methylene]-[2-methyl-6-(2-quinolinylmethoxy)]-3H-indene-1-acetic acid A. p-Methoxy-α-methyl cynnamic acid A mechanically stirred mixture of 4-methoxybenzaldehyde (47.6 g, 0.35 mole), propionic anhydride (78.3 g, 0.602 mole) and sodium propionate (33.5 g, 0.35 mole) is placed under nitrogen in an oil bath heated at 150° C. for 15 hours. Upon addition of water (130 mL) under vigorous stirring a yellow solid is obtained. It is redissolved in 2N-KOH (pH 11) and the solution is extracted with ether. The aqueous phase is acidified (ice bath) with concentrated HCl. The white solid is collected, washed with water and dried to provide the title compound (47.69 g, 71%, m.p. 153°-154° C.).

NMR (DMSO-d$_6$, 400 MHz): δ2.01 (d, J 1.34 Hz, 3H, 2—CH$_3$), 3.77 (s, 3H, OCH$_3$), 6.98 (d, J 8.81 Hz, 2H, ArH), 7.43 (d, J 8.7 Hz, ArH), 7.53 (s, 1H, ArCH=C).

MS (EI, m/z): 192 (b.p., M)$^+$.

Analysis for: C$_{11}$H$_{12}$O$_3$. Calculated: C, 68.74; H, 6.29. Found: C, 68.80; H, 6.43.

B. p-Methoxy-α-methyl hydrocynnamic acid

A mixture of the acid (44 g, 0.229 mole) of Step A, and 10% Pd/C (4.4 g) in dry methanol (500 mL) is hydrogenated overnight at 50 psi. The mixture is filtered (Solka-Floc) and the filtrate evaporated to dryness to yield a pale yellow oil, which is used without further purification (44.5 g).

NMR (CDCl$_3$, 400 MHz): δ1.16 (d, J 6.9 Hz, 3H, 2-CH$_3$), 2.62 (dd, 1H, ArCH) and 2.70 (m, 1H, ArCH), 3.00 (dd, 1H, CH), 3.78 (s, 3H, OCH$_3$), 6.82 (d, 2H, ArH), 7.09 (d, 2H, ArH).

MS (EI, m/z): 194 (M)$^+$, 121 (b.p.).

C. 6-Methoxy-2-methyl-1-indanone

A mechanically stirred mixture of the crude propionic acid (44 g, 0.227 mole) of Step B, is added to warm (50° C.) polyphosphoric acid (420 g). The mixture is then placed in an oil bath heated at 95° C. for 90 minutes (TLC, 9:1 dichloromethane-methanol, UV). The warm mixture is poured into water (3 L) and stirred overnight at room temperature. It is then extracted with ether and ethyl acetate and the combined extracts are washed with saturated NaHCO$_3$ to neutral. The organic phase is washed with brine and dried (MgSO$_4$). Removal of the solvent provides the title compound as an amber oil. It is purified by flash chromatography (on silica Merck-60, dichloromethane as eluent) to yield 25.58 g (64%) of a pale yellow oil.

NMR (CDCl$_3$, 400 MHz): δ1.31 (d, J 7.4 Hz, 3H, 2-CH$_3$), 2.65 (dd, 1H, ArCH) and 2.74 (m, 1H, ArCH), 3.32 (dd, 1H, CH), 3.83 (s, 3H, OCH$_3$), 7.20 (m, 2H, ArH), 7.34 (d, 1H, ArH).

MS (EI, m/z): 176 (M)$^+$, 161 (b.p., M-CH$_3$)$^+$.

D. 6-Hydroxy-2-methyl-1-indanone

To a stirred solution of anhydrous aluminum bromide (69.82 g, 0.261 mole) in anhydrous benzene (250 mL) kept under nitrogen is added dropwise over 30 minutes a solution of the methoxy indanone (18 g, 0.102 mole) of Step C, in benzene (60 mL). The mixture is gently refluxed for 3 hours (TLC, dichloromethane:ethyl acetate 8:2, UV), cooled in an ice bath and treated dropwise with 6N-HCl (ca. 200 mL) to decompose the aluminum complex. The aqueous phase is extracted with ether (3 times), the extracts are concentrated at reduced pressure and extracted with 2.5N-NaOH (2×75 mL and 1×50 mL). The basic extracts are neutralized (ice bath) with concentrated HCl and the oil that separates is extracted with ether (3 times). The combined extracts are washed with brine, dried (MgSO$_4$) and evaporated to yield an oil that readily solidifies. The crude material is flash chromatographed (on silica Merck-60, gradient CH$_2$Cl$_2$, CH$_2$Cl$_2$-ethyl acetate 85:15) to provide the pure title compound (13.60 g, nearly colorless solid, 82%).

NMR (CDCl$_3$, 400 MHz): δ1.31 (d, J 7.44 Hz, 3H, 2-CH$_3$), 2.65 (dd, 1H, ArCH) and 2.76 (m, 1H, ArCH), 3.32 (dd, 1H, CH), 6.68 (s, 1H, OH), 7.18 (dd, 1H, ArH), 7.30 (m, 2H, ArH).

MS (EI, m/z): 162 (M)$^+$, 147 (b.p., M-CH$_3$)$^+$, 133 (M-C$_2$H$_5$)$^+$.

E. 6-(2-Quinolinylmethoxy)-2-methyl-1-indanone

A mixture of the phenol (15.16 g, 93.58 mmole) of Step D, powdered anhydrous potassium carbonate (12.93 g, 93.6 mmole), 18-crown-6 (2.47 g, 9.36 mmole) and dry acetonitrile (200 mL) is stirred at room temperature under a nitrogen for 15 minutes. 2-Chloromethylquinoline (free base, freshly prepared from 18.29 g or 102.96 mmole of the hydrochloride salt) is added in one portion and the mixture is placed in an oil bath heated at 65° C. for 11 hours (TLC, dichloromethane:methanol 9:1, UV). The solvent is removed in vacuo and the residue is partitioned between ethyl acetate and water. The organic phase is washed with brine, dried (MgSO$_4$) and evaporated to yield an oil which solidifies upon trituration with hexane (ca. 31 g). The crude product is purified by flash chromatography (on silica Merck-60, absorbed in methylene chloride, eluted with CH$_2$Cl$_2$-ethyl acetate 90:10 and 85:15) to provide 5.95 g of slightly impure material together with 24.55 g of the pure title compound (pale yellow solid, 84.8%).

NMR (CDCl$_3$, 400 MHz): δ1.29 (d, J 7.36 Hz, 3H, 2-CH$_3$), 2.65 (dd, 1H, ArCH) and 2.73 (m, 1H, ArCH), 3.32 (dd, 1H, CH), 5.41 (s, 2H, ArCH$_2$O), 7.3–7.38 (m, 3H, ArH), 7.55 (t, J ca. 7 Hz, 1H, ArH), 7.64 (d, J 8.5 Hz, 1H, ArH), 7.74 (t, J ca 7 Hz, 1H, ArH), 7.83 (d, J 8 Hz, 1H, ArH), 8.11 (d, J 8.4 Hz, 1H, ArH), 8.20 (d, J 8.4 Hz, 1H, ArH).

MS (EI, m/z): 303 (M)$^+$, 142 (b.p., C$_{10}$H$_8$N)$^+$, 115.

F. 2-Methyl-5-(2-quinolinylmethoxy)-indene-3-acetic acid ethylester

Triethylphosphonoacetate (22.42 g, 100 mmole) is added dropwise under nitrogen to a stirred and cooled (0° C.) slurry of NaH (57% in oil, 4.27 g, 100 mmole) in dry toluene (250 mL). The cooling bath is removed and stirring continued at room temperature for 60 minutes whereby an almost homogeneous solution is obtained. A solution of the indanone (15.15 g, 50 mmole) of Step E, in toluene (50 mL) is then added dropwise. The flask is placed in an oil bath heated at 95° C. for 19 hours (TLC, traces of starting material present, dichloromethane-ethyl acetate 9:1, UV, Vaughn's). The reddish solution is cooled, diluted with water and extracted with ethyl acetate (3 times). The combined extracts are washed with brine, dried (anhydrous K$_2$CO$_3$) and evaporated to dryness. The residue (heavy brown oil) is flash chromatographed (on silica Merck-60, eluted using a gradient dichloromethane→dichloromethane:ethyl acetate 84:16) to provide the title compound as a mixture of endo and exo isomers (16.3 g, 87.4%, oil that solidifies upon standing) together with unreacted, more polar starting material (1.84 g, 12% recovery).

MS (EI, m/z): 373 (M)$^+$, 344 (M-C$_2$H$_5$)$^+$, 300 (M-COOC$_2$H$_5$)$^+$, 143 (b.p.), 115.

G. 3-[(4-Chlorophenyl)methylene]-[2-methyl-6-(2-quinolinylmethoxy)]-3H-indene-1-acetic acid To a vigorously stirred mixture of the ester (mixture of isomers, 6.9 g, 18.5 mmole) prepared as described in Step F, and p-chlorobenzaldehyde (2.86 g, 20.3 mmole, 1.1 equiv.) in dry methanol (45 mL) is added dropwise under nitrogen 25% methanolic sodium methoxide (8 mL, 2 equiv.). The mixture is warmed until it becomes homogeneous (ca. 65° C., bath temp.) and then refluxed for a total of 13 hours. After overnight at room temperature, the slurry (bright yellow precipitate) is treated dropwise with water (35 mL) and a little methanol and refluxing is continued for another 4 hours (reaction followed by TLC). The dark orange solution is cooled, the methanol evaporated, more water added and the gelatinous precipitate is collected, washed with water and dried to provide the sodium salt of the title compound as a bright yellow solid. The latter is slurried in water and neutralized (to pH 6–6.5) with 10% acetic acid. The mixture is extracted with ethyl acetate (large volume), the extract is washed with brine and evaporated to dryness. The residue is azeotroped with benzene to provide an orange solid [7.52 g, mixture of Z (major) and E (minor) isomers]. This material is slurried in ether, stirred for 30 minutes, filtered and dried (4.32 g). The solid is extracted portionwise with hot ethyl acetate (containing some methanol and dichloromethane) until almost completely dissolved. The filtrate is concentrated in vacuo until precipitation occurs, diluted with ether and the yellow solid collected and dried (3.1 g, m.p. 218°–220° C.). Concentration of the mother liquors provides additional product (1.1 g, m.p. 200°–203° C.). Combined yield is 4.4 g (51%). The NMR spectrum is consistent [see: Shuman et al., *J. Org. Chem.*, 42, 1914, (1977)] with the Z-isomer.

NMR (DMSO-d$_6$, 400 MHz): δ2.11 (s, 3H, CCH$_3$), 3.54 (s, 2H, CH$_2$COO), 5.326 (s, 2H, OCH$_2$Ar), 6.60 (dd, 1H ArH), 6.95 (d, J 2.35 Hz, 1H), 7.14 (m, 2H, ArH), 7.52 (m, 4H, ArH), 7.60 (t, J 7.03 Hz, 1H, ArH), 7.66 (d, J 8.39 Hz, 1H, ArH), 7.77 (t, 1H, ArH), 7.99 (m, 2H, ArH), 8.4 (d, J=8.9 Hz, 1H, ArH).

UV (λmax, MeOH, nm): 232 (ε39,594), 285.2 (14,830), 287.8 (14,921), 288 (14,921), 338.2 (10,839).

MS (+FAB, m/z): 468 (1Cl, M+H)$^+$, 237,131,91 (b.p.).

Analysis for: C$_{29}$H$_{22}$ClNO$_3$ Calculated: C, 74.43; H, 4.74; N, 2.99. Found: C, 74.54; H, 4.67; N, 3.13.

EXAMPLE 2

2-Methyl-3-[[4-(methylthio)phenyl]methylene]-6-(2-quinolinylmethoxy)-3H-indene-1-acetic acid To a vigorously stirred mixture of the ester (mixture of isomers, 6.7 g, 17.96 mmole), prepared as described in Example 1, Step F, and (4-methylthio)benzaldehyde (3.05 g, 19.06 mmole, 1.1 equiv.) in dry methanol (75 mL) is added dropwise under nitrogen 25% methanolic sodium methoxide (7.7 mL, 2 equiv.). The mixture is warmed until it becomes homogeneous (ca. 65° C., bath temp.) and then refluxed for a total of 13 hours (TLC, $CH_2Cl_2$-ethyl acetate 9:1). After overnight at room temperature, the slurry (bright yellow precipitate) is treated dropwise with water (65 mL) and a little methanol and refluxing is continued for another 5.5 hours (reaction followed by TLC). The brown solution is cooled, the methanol evaporated, more water added and the gelatinous precipitate is collected, washed with water and dried to provide the sodium salt of the title compound as a yellow solid. The latter is slurried in water and neutralized (to pH 6-6.5) with 10% acetic acid. The mixture is extracted with ethyl acetate (large volume), the extract is washed with brine and evaporated to dryness. The residue is azeotroped with benzene to provide a yellow solid (4.47 g, 52%). This material is slurried in ether, stirred for 30 minutes, filtered and dried (4.13 g, m.p. 205°-207° C., dec.). The solid is extracted portionwise with hot ethyl acetate (containing some methanol and dichloromethane) until almost completely dissolved. The filtrate is concentrated in vacuo until precipitation occurs and diluted with ether. The yellow solid is collected and dried (3.5 g, 35.4%, m.p. 207°-209° C., dec.). The NMR spectrum is consistent [see: Shuman et al., *J. Org. Chem.*, 42, 1914, (1977)] with the Z-isomer.

NMR (DMSO-$d_6$, 400 MHz): $\delta$2.11 (s, 3H, $CCH_3$), 2.51 (s, 3H, $SCH_3$), 3.53 (s, 2H, $CH_2COO$), 5.32 (s, 2H, $OCH_2Ar$), 6.60 (dd, 1H, ArH), 6.95 (d, 1H, J 2.35 Hz), 7.13 (s, 1H, ArH), 7.30 (m, 3H, ArH), 7.47 (d, 2H, J 8.4 Hz, ArH), 7.60 (t, J 7.0 Hz, 1H, ArH), 7.66 (d, 1H, J 8.49 Hz, ArH), 7.77 (t, 1H, J ca. 7 Hz, ArH), 7.99 (m, 2H, ArH), 8.4 (d, 1H, J 8.49 Hz, ArH).

UV ($\lambda$max, MeOH, nm): 231.5 ($\epsilon$37,382), 303 (9,739), 307.5 (9,342), 315 (10,525), 352.5 (13,407).

MS (+FAB), m/z): 480 (M+H)+.

Analysis for: $C_{30}H_{25}NO_3S$ Calculated: C, 75.13; H, 5.25; N, 2.92. Found: C, 75.30; H, 5.25; N, 2.95.

EXAMPLE 3

2-Methyl-3-[[(4-methylsulfinyl)phenyl]methylene]-6-(2-quinolylmethoxy)-3H-indene-1-acetic acid monohydrate A slurry of the thioether (1.67 g, 3.48 mmole) of Example 2 in a cold mixture of chloroform and glacial acetic acid (65:35, 40 mL) is treated dropwise (via syringe) with 30% $H_2O_2$ (0.403 mL). The mixture is stirred for 30 minutes in the cold and then at room temperature for 24 hours. A clear solution is obtained after 2 hours and a small amount of $H_2O_2$ is added after 4 and 7 hours, respectively, to drive the reaction to completion (reaction followed by TLC, aliquot treated with water and extracted with ethyl acetate). The chloroform is evaporated, the residue is diluted with water and neutralized in the cold with the calculated amount of $NH_4OH$. The precipitate is filtered, slurried in water, collected, washed with water and dried in vacuo (over $P_2O_5$) to yield the crude acid as a yellow solid. The solid is redissolved in a large volume of warm (30°-35° C.) ethyl acetate (containing some methanol and dichloromethane) and filtered. The filtrate is concentrated in vacuo until precipitation starts and diluted with ether. The precipitate is collected, washed with ether and dried (fluffy solid, m.p. 136°-137° C., sintering and foaming).

NMR (DMSO-$d_6$, 400 MHz): $\delta$2.12 (s, 3H, 2—$CH_3$), 2.80 (s, 3H, $SOCH_3$), 3.55 (s, 2H, $CH_2COO$), 5.32 (s, 2H, $ArCH_2O$), 6.58 (dd, 1H, ArH), 6.96 (d, J 2.3 Hz, 1H), 7.14 (d, J 8.36 Hz, 1H, ArH), 7.21 (s, 1H, ArH), 7.58-7.80 (m 7H, ArH), 7.98 (m, 2H, ArH), 8.39 (d, J 8.5 Hz, 1H, ArH), 12.36 (s, 1H, COOH).

MS (+FAB, m/z): 518 (M+Na)+, 496 (M+H)+.

Analysis for: $C_{30}H_{25}NO_4S.H_2O$ Calculated: C, 70.19; H, 5.30; H, 2.73. Found: C, 69.15; H, 4.93; N, 2.65.

EXAMPLE 4

5-Fluoro-2-methyl-1-[[4-(2-quinolinylmethoxy)phenyl]-methylene]-1H-indene-3-acetic acid A. 4-[(2-quinolinyl)-methoxy]-benzaldehyde To a solution of sodium metal (0.9 g, 39.13 g.a.) in absolute ethanol (50 mL) is added dropwise under nitrogen a solution of 4-hydroxybenzaldehyde (5 g, 40.94 mmole) in absolute ethanol (50 mL). The mixture is gently refluxed for 1 hour and then treated dropwise with a solution of 2-chloromethylquinoline (free base, 7.24 g, 40.76 mmole), freshly prepared from the HCl salt) in ethanol (50 mL). The mixture is refluxed for 24 hours, the solvent is evaporated and the residue is partitioned between water and ethyl acetate. The organic layer is washed with 5% NaOH (pH 8), water, brine to neutral and dried (MgSO$_4$). Removal of the solvent yields the title compound as a yellow solid (9.81 g). The crude material is further purified by flash chromatography (on silica Merck-60, hexane-ethyl acetate 9:1 to remove less polar impurities and 8:2 to elute the product). Yield: 7.37 g (71.5%), m.p. 82°-83° C.

NMR (CDCl$_3$, 200 MHz): $\delta$5.5 (s, 2H, ArCH$_2$O), 7.2-8.6 (m, 9H, ArH), 9.80 (s, 1H, CHO).

B. 5-Fluoro-2-methyl-1-[[4-(2-quinolinylmethoxy)-phenyl]methylene]-1H-indene-3-acetic acid To a mixture of 5-fluoro-2-methyl-indene-3-acetic acid (prepared according to the procedure disclosed in U.S. Pat. No. 3,654,349) (2 g, 9.7 mmole) and the aldehyde (3.2 g, 12.19 mmole) of Step A, in dry methanol (40 mL) is added dropwise under nitrogen 25% methanolic sodium methoxide (6.48 mL). The mixture is warmed until homogeneous and then refluxed for a total of 16 hours. The solvent is evaporated and the residue is slurried in water. The gelatinous precipitate is collected, washed with water and dried. It is then slurried in ether, filtered and dried to provide the sodium salt of the title compound as a yellow solid (2.03 g, 46.3%). The salt is slurried in water and neutralized (to pH 6-6.5) with 10% acetic acid. The acid is extracted with ethyl acetate (large volume), dried (MgSO$_4$) and evaporated to dryness. The crude acid is recrystallized from a hot mixture of methanol and ethanol (large volume needed to dissolve, concentrate to smaller volume after filtration). The analytical sample is dried overnight in vacuo at 35° C. The yellow solid (m.p. 218°-221° C., dec) is a mixture of Z and E isomers in approximately 6:1 ratio (NMR).

NMR (DMSO-$d_6$, 400 MHz): $\delta$1.84 (s, 2-CH$_3$, minor E isomer), 2.12 (s, 2—CH$_3$, major Z isomer), 3.55 (s, 2H, CH$_2$COO), 5.41 (s, ArCH$_2$O, possibly E isomer), 5.44 (s, ArCH$_2$O, possibly Z isomer), 6.70 (dt, 1H, ArH), 6.85-7.3 (m, 1H, ArH), 7.18 (d, 2H, J 8.7 Hz, ArH), 7.28 (s, 1H, ArH), 7.32-7.40 (m, 1H, ArH), 7.51 (d, 2H, J 8.6 Hz, ArH), 7.62 (t, 1H, J ca. 7 Hz, ArH), 7.68-7.76 (m, 1H, ArH), 7.79 (t, J, 7 Hz, 1H, ArH), 8.01 (nm, 2H, ArH), 8.44 (d, 1H, 8.5 Hz, ArH), 12.4 (broad s, 1H, COOH).

MS (Cl, m/z): 452 (M+H)+, 408 (M—COOH)+.
Analysis for: $C_{29}H_{22}FNO_3$ Calculated: C, 77.15; H, 4.91; N, 3.10. Found: C, 77.08; H, 4.93; N, 3.12.

EXAMPLE 5

2-Methyl-3-[[4-(methylthio)phenyl]methylene]-6-[(2-naphthyl)methoxy]-3-H-indene-1-acetic acid A. 6-[(2-Naphthyl)methoxy]-2-methyl-indanone A mixture of the indanone (14 g, 86.4 mmole) prepared as described in Example 1, Step D, anhydrous $K_2CO_3$ (11.24 g, 81.4 mmole), 18-crown-6 (2.29 g, 6.4 mmole) and 2-bromomethylnaphthalene (11.6 g, 95 mmole) in acetonitrile (275 mL) is heated under nitrogen for 24 hours (in an oil bath set at 70° C.). The acetonitrile is evaporated and the residue is dissolved in water, extracted with ethyl acetate, dried ($MgSO_4$) and evaporated to dryness. The crude product (tan solid) is flash chromatographed (on silica Merck-60, preabsorbed in $CH_2Cl_2$, eluted with 8:2 hexane-ethyl acetate) to provide the title compound as a white solid (13.49 g, 52%).

NMR ($CDCl_3$, 400 MHz): δ1.30 (d, J 3.2 Hz, 3H, 2-$CH_3$), 2.70 (m, 2H, Ar$CH_2$C), 3.35 (m, 1H, CHCO), 5.25 (s, 2H, Ar$CH_2$O), 7.32 (m, 3H, ArH), 7.50 (m, 3H, ArH), 7.85 (m, 4H, ArH).

MS (EI, m/z): 302 (M)+, 141.

B. I) 6-[(2-Naphthyl)methoxy]-2-methyl-indan-1-ylidene-acetic acid ethylester (Z isomer)
II) 6-[(2-Naphthyl)methoxy]-2-methyl-indan-1-ylidene-acetic acid ethylester (E isomer)
III) 5-[(2-Naphthyl)methoxy]-2-methyl-indene-3-acetic acid ethyl ester Triethylphosphonoacetate (19.8 g, 88.3 mmole) is added dropwise under nitrogen to a stirred and cooled suspension of NaH (60% in oil, 3.53 g, 88.2 mmole) in toluene (225 mL). The cooling bath is removed. A clear solution is obtained after 10 minutes at room temperature. A solution of the indanone (13.3 g, 44 mmole) of Step A, in toluene (40 mL) is added dropwise and the mixture is placed in an oil bath heated at 100° C. for 54 hours (follow by TLC, hexane-ethyl acetate 7:3). Water is added, the layers are separated and the aqueous phase is reextracted with ethyl acetate (3 times). The extracts are dried ($K_2CO_3$) and evaporated to dryness to yield the crude product as an amber oil (21.5 g), mixture of endo and exo isomers. Flash chromatography of this crude material (on silica Merck-60, preabsorbed in $CH_2Cl_2$, hexane-ethyl acetate 9:1) provides small amounts of each of the pure isomers (i.e. I, II and III) together with mixed fractions and unreacted starting material (ca. 5.24 g). The structures of the isomers are confirmed by MS and NMR and assigned by NOE. The mixture of endo and exo esters is routinely used in the next step (combined yield 8.94 g or 54.7%; 90% based upon recovered starting material).

Isomer I
NMR ($CDCl_3$, 400 MHz): δ1.26 (d, J 6.8 Hz, 3H, 2-$CH_3$), 1.32 (t, J 7 Hz, 3H, ester $CH_3$), 2.54 (d, J 15.1 Hz, 1H, ArCHC), 3.1 (m, 2H, ArCHC+CCH), 4.22 (q, J 7.2 Hz, 2H, ester $CH_2$), 5.28 (s, 2H, Ar$CH_2$O), 5.85 (s, 1H, C═CH—COO), 7.04 (dd, 1H, J 8.4 Hz and 2.5 Hz, ArH), 7.17 (d, J 8.4 Hz, 1H, ArH), 7.49 (m, 2H, ArH), 7.59 (d, J 8.4 Hz, 1H, ArH), 7.82 (m, 3H, ArH), 7.95 (s, 1H, ArH), 8.61 (s, 1H, ArH).

MS (EI, m/z): 372 (M)+, 231, 141 (b.p.).

Isomer II
NMR ($CDCl_3$, 400 MHz): δ1.21 (d, 3H, J 7 Hz, 2-$CH_3$), 1.33 (t, 3H, J 7.1 Hz, ester $CH_3$), 2.56 (d, J 16.3 Hz, 1H, ArCHC), 3.18 (dd, J 16.3 and 7.1 Hz, 1H, ArCHC), 3.88 (m, 1H, CCH), 4.22 (q, J ca. 7 Hz, 2H, ester $CH_2$), 5.24 (s, 2H, Ar$CH_2$O), 6.19 (s, 1H, C═C—COOEt), 7.06 (dd, J 8.4 and 2.4 Hz, 1H, ArH), 7.17 (d, J 2.3 Hz, 1H, ArH), 7.23 (d, J 8.4 Hz, 1H, ArH), 7.49 (m, 2H, ArH), 7.54 (dd, J 8.4 and 1.6 Hz, 1H, ArH), 7.88 (m, 4H, ArH).

MS (CI, m/z): 373 (M+H)+, 261 (b.p.), 233

Isomer III
NMR ($CDCl_3$, 400 MHz): δ1.20 (t, J 7 Hz, 3H, ester $CH_3$), 2.11 (s, 3H, 2—$CH_3$). 3.28 (s, 2H, Ar$CH_2$), 3.48 (s, 2H, $CH_2$COO), 4.09 (q, J 7.1 Hz, 2H ester $CH_2$), 5.25 (s, 2H, Ar$CH_2$O), 6.79 (dd, J 8.1 and 2.3 Hz, 1H, ArH), 6.98 (s, 1H, ArH), 7.24 (d, 8.8 Hz, 1H, ArH), 7.48 (m, 2H, ArH), 7.56 (dd, J 8.4 and 1.7 Hz, 1H, ArH), 7.87 (m, 4H, ArH).

MS (CI, m/z): 373 (M+H)+, 285

C. 2-Methyl-3-[[4-(methylthio)phenyl]methylene]-6-[(2-naphthyl)methoxy]-3H-indene-1-acetic acid Tp a mixture of the ester (mixture of isomers prepared as described above (2.5 g, 6.71 mmole) and 4-(methylthio)-benzaldehyde (1.124 g, 7.38 mmole) in anhydrous methanol (60 mL) is added dropwise under nitrogen 25 % methanolic sodium methoxide (2.9 mL). The mixture is refluxed for 16 hours, the solvent removed and the residue slurried in water and stirred overnight (the initial yellow oil turns into a solid). The water is evaporated in vacuo and the residue is triturated with ether (to remove unreacted aldehyde), filtered, washed with ether and dried(yellow solid, 2.65 g). The crude sodium salt is slurried in water and acidified (to pH 6.5) with 10% acetic acid. The acid is collected, washed and dried in vacuo. It is again washed with ether and dried (1.02 g, 32%, m.p. 209°–211° C., dec.). The NMR shows it to be a mixture of Z and E isomers in approximately 8:1 ratio.

NMR (DMSO-$d_6$, 400 MHz): δ1.81 (s, 2—$CH_3$, minor isomer E), 2.11 (s, 2—$CH_3$, major isomer Z), 2.51 (s, 3H, $SCH_3$), 3.54 (s, 2H, $CH_2$COO), 5.23 (s, Ar$CH_2$O, Z isomer) and 5.28 (s, Ar$CH_2$O, E isomer), 6.60 (dd, 1H, ArH), 6.90 (d, J 2.2 Hz, 1H, ArH), 7.12 (s, 1H, ArH), 7.27-7.36 (m, 3H, ArH), 7.46-7.62 (m, 5H, ArH), 7.88-8.00 (m, 4H, ArH), 12.33 (broad s, 1H, COOH).

MS (CI, m/z): 479 (M+H)+, 435 (M+H-COO)+, 141 ($C_{11}H_9$, naphthyl)+.

Analysis for: $C_{31}H_{26}O_3S$ Calculated: C, 77.80; H, 5.48. Found: C, 77.44; H, 5.47.

EXAMPLE 6

3-[(4-Chlorophenyl)methylene]-[2-methyl-6-(2-quinolinylmethoxy)]-3H-indene-1-acetic acid A. 5-Hydroxy-2-methyl indene-3-acetic acid A mixture of the indanone (1.81 g, 11.17 mmole) of Example 1, Step D, cyanoacetic acid (1.05 g, 12.3 mmol) ammonium acetate (0.17 g), acetic acid (0.66 g) and toluene (5 mL) is heated at reflux with water removal (Dean-Stark) for 24 hours (TLC, $CH_2Cl_2$-ethyl acetate 8:2). The toluene is evaporated and the residual yellow solid is redissolved in ethanol (6 mL) containing 2.2 N-KOH (1.4 mL). A solution of KOH (2.2 g, 85) in water (15 mL) is added and the solution is refluxed under nitrogen for 18 hours. The ethanol is evaporated, the residue is diluted with water and extracted with ether (2 times). The aqueous layer is acidified in the cold with 6N-HCl (to pH 3) and extracted with ethyl acetate. The extracts are washed with brine, dried ($MgSO_4$) and evaporated to provide the crude title compound together with traces of unreacted indanone. It is used as such in the next step.

NMR (DMSO-d$_6$, 200 MHz): δ2.02 (s, 3H, 2—CH$_3$), 3.2 (s, 2H, ArCH$_2$), 3.4 (s, 2H, CH$_2$COO), 6.48 (d, 1H, ArH), 6.6 (s, 1H, ArH), 7.1 (d, 1H, ArH), 9.08 (broad, 1H, OH).

B. 5-Hydroxy-2-methyl-indene-3-acetic acid methylester

To a solution of the crude acid as prepared in Step A, above, in dry methanol (120 mL) is added p-toluenesulfonic acid monohydrate (1.9 g) and the mixture is gently refluxed for 1.5 hours. The methanol is evaporated, the residue dissolved in ethyl acetate, washed with brine and dried (MgSO$_4$). Removal of the solvent provides a brown oil that readily solidifies upon drying in vacuo. The residue is flash chromatographed (silica Merck-60, absorbed in dichloromethane, eluted with dichloromethane-ethylacetate 98:2 and 94:6) to yield the pure title compound as an offwhite solid (9.4 g, 80%).

NMR (CDCl$_3$, 400 MHz): δ2.1 (s, 3H, 2—CH$_3$), 3.26 (s, 2H, ArCH$_2$), 3.49 (s, 2H, CH$_2$COO), 3.67 (s, 3H, COOCH$_3$), 4.89 (broad s, OH), 6.59 (dd, 1H, ArH), 6.75 (d, 1H, J 2.4 Hz, ArH), 7.18 (d, 1H, 7.9 Hz, ArH).

MS (EI, m/z): 218 (M)$^+$, 158 (b.p.).

C. 3-[(4-Chlorophenyl)methylene]-[2-methyl-6-hydroxy]-3H-indene-1-acetic acid

To a solution of sodium metal (0.170 g, 7.39 g.a.) in anhydrous methanol (2.5 mL) under nitrogen is added dropwise with cooling a solution of the ester (0.537 g, 2.46 mmole) of step B, in methanol (5 mL) followed by p-chlorobenzaldehyde (0.381 g, 2.71 mmole, 1.1 equiv.). The mixture is stirred in an oil bath heated at 65°–70° C. for 6 hours followed by standing overnight at room temperature (TLC, CH$_2$Cl$_2$-ethyl acetate 93:7). Water (10 mL) and methanol (2 mL) are added and the mixture is again refluxed under nitrogen for 3 hours (TLC, CH$_2$Cl$_2$-ethyl acetate 90:10). The methanol is evaporated, the residue is dissolved in water, and washed with ether (2 times). The aqueous phase is acidified in the cold with 6N-HCl (to pH 3) and extracted with ethyl acetate. The extracts are washed (brine) and evaporated to yield a greenish-yellowish solid (0.8 g). The NMR spectrum shows that it is a mixture of the title compound and 5-hydroxy-2-methyl-indene-3-acetic acid. They are best separated as their methylesters (see below).

D. 3-[(4-Chlorophenyl)methylene]-[2-methyl-6-hydroxy[-3H-indene-1-acetic acid methylester A solution of the crude acids (2.46 mmole, obtained as described in Step C, above) in methanol (10 mL) containing p-toluenesulfonic acid monohydrate (60 mg) is refluxed for 5 hours. The methanol is evaporated and the residue dissolved in ethyl acetate, washed with brine and dried (MgSO$_4$). The solvent is evaporated and the residue is flash chromatographed (on silica Merck-60, absorbed in 1:1 dichloromethane-hexane, eluted with toluene-isopropanol 95:5) to provide the title compound (less polar spot, 0.103 g, yellow solid) together with some impure material (0.390 g, oil that solidifies upon standing). The Z configuration is confirmed by NOE. The more polar spot is identical (NMR, TLC) with methyl-5-hydroxy-2-methylindene-3-acetate.

NMR (CDCl$_3$, 400 MHz): δ2.17 (s, 3H, 2—CH$_3$), 3.55 (s, 2H, CH$_2$COO), 3.69 (s, 3H, COOCH$_3$), 6.33 (dd, 1H, ArH), 6.67 (d, J 2.3 Hz, 1H, ArH), 7.01 (s, 1H), 7.14 (d, J 8.3 Hz, 1H, ArH), 7.40 (dd, 4H, ArH).

MS (EI, m/z): 342/340 (1 Cl, M)$^+$, 231 (b.p.)

E. 3-[(4-Chlorophenyl)methylene]-[2-methyl-6-(2-quinolinylmethoxy)]-3H-indene-1-acetic acid methylester A mixture of the ester (0.410 g, 1.2 mmole) of Step D, anhydrous potassium carbonate (0.17 g), and 18-crown-6 (0.050 g) in acetonitrile (7 mL) is stirred at room temperature for 15 minutes. 2-Chloromethylquinoline is added (free base, 0.149 g, 1.42 mmole, freshly prepared from the hydrochloride salt) and the deep red mixture is stirred under nitrogen for 15 hours in an oil bath heated at 65° C. A 10% excess of potassium carbonate, crown ether and the 2-chloromethylquinoline is then added and the reflux is continued for another 2 hours (TLC, hexane-isopropanol 93:7). The solvent is evaporated and the residue is partitioned between water and ethyl acetate. The organic phase is washed (brine), dried (MgSO$_4$) and evaporated to dryness. The crude product is identical (NMR, TLC) with the material described in Example 7, below.

F. 3-[(4-Chlorophenyl)methylene]-[2-methyl-6-(2-quinolinylmethoxy)]-3H-indene-1-acetic acid 1N-KOH (3.72 mL) is added dropwise to a warm solution of the ester (0.600 g, 1.24 mmole) of Step E, in methanol (7 mL). The mixture is refluxed under nitrogen for 3 hours. After stirring overnight at room temperature (TLC, hexane-isopropanol 93:7), the methanol is evaporated and the residue washed with ether. The solid is slurried in water, neutralized in the cold with 10% acetic acid (to pH 6–6.5) and extracted with ethyl acetate (vigorous stirring is necessary to achieve solution). The extracts are washed with brine, dried (MgSO$_4$) and evaporated to yield the crude acid (0.250 g, 43%). It is recrystallized from hot ethyl acetate/methylene chloride (dissolve in a large volume and concentrate the filtrate until precipitation occurs). The pure title compound (m.p. 216°–218° C.) is identical (TLC, NMR) with the material described in Example 1, Step G. (Z isomer).

EXAMPLE 7

3-[(4-Chlorophenyl)methylene]-[2-methyl-6-(2-quinolinylmethoxy)]-3H-indene-1-acetic acid methylester A suspension of the acid (1.88 mmole, crude material before purification, obtained as described in Example 1, Step G), in methanolic HCl (15 mL) is refluxed until the reaction is complete by TLC (dichloromethane-methanol 9:1, UV). The methanol is evaporated and the residue is partitioned between ethyl acetate and dilute NH$_4$OH. The extracts are washed with brine, dried (K$_2$CO$_3$) and evaporated to dryness to provide a yellow oil that foams in vacuo (0.900 g). The crude product is flash chromatographed (on silica Merck-60, toluene-hexane-isopropanol 50:50:1 as eluent) to yield the pure title compound (0.630 g, yellow foam that solidifies upon trituration with ethanol, 69.6% over 2 steps). Mixture of Z and E isomers in approximately 4:1 ratio (based upon the position of the 2—CH$_3$ signal in the NMR spectrum).

NMR (CDCl$_3$, 400 MHz): δ1.81 (s, 2—CH$_3$, minor isomer E), 2.17 (s, 2—CH$_3$, major isomer Z), 3.56 (s, 2H, CH$_2$COO), 3.62 (s, 3H, OCH$_3$) 5.42 (s, 2H, ArOCH$_2$), 6.52 (dd, 1H, ArH), 6.89 (d, J 2.4 Hz, 1H), 7–8.3 (m, 12H, ArH).

MS (+FAB, m/z): 482 (1Cl, M+H)$^+$, 360, 217, 143 (b.p.)$^+$, 91.

EXAMPLE 8

1,8-Diethyl-1,3,4,9-tetrahydro-6-(2-quinolinylmethoxy)pyrano[3,4-b]indole-1-acetic acid A. 7-Ethyl-2,3-dihydrotryptophol A mixture consisting of 7-ethyltryptophol (28.0 g, 0.148 mol) and 250 mL of trifluoroacetic acid is stirred at room temperature. Sodium borohydride pellets (5.4 g, 0.145 mol) are added over a 4 hour period. After addition is complete, the reaction is stirred for 1 hour. The reaction mixture is poured onto ice and neutralized with 50% NaOH to pH 10. The aqueous layer is extracted with ether (3×200 mL). The ether layers are combined and extracted with 5% HCl solution (3×200 mL). The combined acidic solution is then made alkaline with 50% NaOH and extracted with ether (3×200 mL). The combined ether layers are washed with water (2×200 mL), once with brine (200 mL), dried (MgSO$_4$), filtered and concentrated to afford 17.3 g of oil. Flash chromatography using 60% ethyl acetate/hexane, and then 80% ethyl acetate/hexane affords 13.5 g of solid title compound, m.p. 73°–75° C.

NMR (CDCl$_3$): δ6.98 (d, J=8.3 Hz, 1H, Ar), 6.93 (d, J=5.3 Hz, 1H, Ar), 6.74 (t, J=7.5 Hz, 1H, Ar), 3.7 (m, 3H, OCH$_2$OH), 3.68 (m, 2H, NH—CH$_2$), 3.56 (m, 1H), 3.33 (m, 1H, NH—CH$_2$), 2.49 (q, J-7.6 Hz, 2H, CH$_2$CH$_3$), 2.11 (m, 1H, CH$_2$CH$_2$), 1.80 (m, 1H, CH$_2$CH$_2$), 1.21 (t, J=7.6 Hz, CH$_2$CC3).

MS: m/e 191 (M+), 130, 118.

B. 7-Ethyl-5-hydroxytryptophol

A solution of potassium nitrosodisulfonate (17.0 g, 0.063 mol) in pH 7 buffer (760 mL) is added over a 20 minute period to a stirring solution of 7-ethyl-2,3-dihydrotryptophol (5.0 g, 0.026 mol) in 350 mL of acetone. Ten minutes after the addition is complete, the reaction mixture is extracted with ethyl acetate (4×300 mL). The combined ethyl acetate layers are washed with distilled water (2×200 mL), once with brine (200 mL), dried (MgSO$_4$) and concentrated to afford 5.6 g of crude product. The crude product is loaded onto a flash chromatography column. The next day, it is flashed using 70% ethyl acetate/hexane to afford 2.5 g of title compound.

NMR (DMSO-d$_6$): δ8.43 (s, 1H, 6.97 (d, J=2.3 Hz, 2H, arom), 6.60 (d, J=2.1 Hz, 1H, arom), 6.40 (d, J-2,1 Hz, 1H, arom), 4.55 (t, J-5.3 Hz, 1H, CH$_2$OH), 3.57 (m, 2H), 3.32 (s, 1H, Ar-OH), 2.7 (m, 4H), 1.20 (t, J=7.5 Hz, 3H).

MS: 205 (M)+, 174, 159.

Analysis for: C$_{12}$H$_{15}$NO$_2$ Calculated: C, 70.22; H, 7.37; N, 6.82. Found: C, 70.15; H, 7.52; N, 6.60.

C. 1,8-Diethyl-1,3,4,9-tetrahydro-6-hydroxypyrano[3,4-b]indole-1-acetic acid methyl ester A mixture consisting of 7-ethyl-5-hydroxytryptophol (15.5 g, 0.076 mol), 20% tetrahydrofuran/methylene chloride (1200 mL), methyl 3-methoxy-2-pentenoate (17.5 g, 0.0121 mol) and boron trifluoride etherate (23.0 mL, 0.187 mol) is stirred at room temperature for 28 hours. The reaction mixture is diluted with 100 mL of methylene chloride and washed with 5% NaHCO$_3$ (3×500 mL), once with water, dried (MgSO$_4$) and concentrated to give 30.3 g of crude. Flash chromatography using 25% ethyl acetate/hexane as an eluent afforded 16.0 g of title compound, m.p. 153°–154° C.

NMR (CDCl$_3$): δ8.90 (bs, 1H), 6.74 (d, J=23 Hz, H, arom), 6.49 (d, J=2.4 Hz, 1H, arom), 4.50 (s, 1H, Ar-OH), 4.00 (m, 2H), 3.7 (s, 3H), 3.0–2.70 (m, 6H), 2.20 (m, 2H), 1.33 (t, J=7.6 Hz, 3H), 0.82 (t, J=7.6 Hz, 3H).

MS: 317 (M)+, 288, 244.

Analysis for: C$_{18}$H$_{23}$NO$_4$ Calculated: C, 68.12; H, 7.30; N, 4.41. Found: C, 67.73; H, 7.23; N, 4.24.

D. 1,8-Diethyl-1,3,4,9-tetrahydro-6-hydroxypyrano[3,4-b]indole-1-acetic acid

A mixture consisting of the methyl ester (43.1 g, 0.136 mol) of Step C, potassium hydroxide (2.4 g, 0.407 mol), 1600 mL of methanol and 160 mL water is refluxed for 5 hours under a nitrogen atmosphere. The excess methanol is evaporated and water (1000 mL) is added to the residue. The mixture is extracted with ether (3×500 mL). The aqueous layer is made acidic with 5% HCl (pH 2), then extracted with chloroform (4×300 mL). The combined chloroform layers are washed with water (2×500 mL), brine (500 mL), dried (MgSO$_4$), and concentrated under vacuo to yield 43.0 g of foam. Flash chromatography using 15% acetone/toluene as eluent, affords 40.0 g of foam. This is crystallized from acetonitrile/toluene to afford 35.4 g of pure title compound, m.p. 172°–173° C.

$^1$H NMR (DMSO-d$_6$): δ8.44 (s, 1H, —NH), 6.51 (d, J=2.1 Hz, 1H, Ar), 6.39 (d, J=1.96 Hz, 1H, Ar), 3.89 (m, 2H), 2.89 (q, 2H), 2.87 (d, J=13.5 Hz, 1H, CH$_2$COOH), 2.75 (d, J=15.8 Hz, 1H, CH$_2$COOH), 2.71–2.57 (m, 2H), 1.99 (q, J=7.2 Hz, 2H), 1.20 (t, J=7.6 Hz, 3H), 0.60 (t, J=8.5 Hz, 3H).

IR (KBr, cm$^{-1}$): 3590 (OH), 1720 (CO).

UV (MeOH, nm): 276 (9940), 295 (6400).

MS: m/e 303 (M+), 244.

Analysis for: C$_{17}$H$_{21}$NO$_4$ Calculated: C, 67.31; H, 6.98; N, 4.62. Found: C, 66.99; H, 6.80; N, 4.96.

E. 1,8-Diethyl-1,3,4,9-tetrahydro-6-(2-quinolinylmethoxy)pyrano[3,4-b]indole-1-acetic acid A mixture consisting of 1,8-diethyl-1,3,4,9-tetrahydro-6-hydroxypyrano[3,4-b]indole acetic acid methyl ester (5.0 g, 0.0158 mol), dimethylsulfoxide (250 mL), and potassium iodide (150 mg) is stirred at room temperature. A solution of sodium hydroxide (3.9 g, in 20 mL H$_2$O) is added and stirred at room temperature followed by addition of 2-chloromethyl quinoline hydrochloride (8.4 g, 0.0392 mol). The reaction mixture is heated at 70°–80° C. for 3.5 hours, cooled and diluted with water (100 mL). The mixture is made acidic with 1N HCl to pH 4, and extracted with ethyl acetate (3×400 mL). The combined organic layers are washed with water (3×200 mL), once with brine (200 mL), dried over MgSO$_4$, filtered and concentrated to give 10.0 g of crude product. The crude product is chromatographed on silica gel using 7% methanol/methylene chloride as eluent to afford 2.9 g pure product. The latter is dissolved in 200 cc ethyl acetate and precipitated by dropwise addition to petroleum ether (700 mL) to afford 2.7 g of the title compound, m.p. 179°–181° C.

$^1$H NMR (400 MHz, DMSO-d$_6$): δ8.38 (d, J=8.5 1H, 4Q), 8.0 (d, J=8.6 1H, 8Q), 7.97 (d, J-7.2, 1H–5Q), 7.76 (dt, J$_1$=6.8, J$_2$=1.5 1H, 7Q), 7.70 (d, J=8.5 1H, 3Q), 7.58 (dt, J$_1$=6.9, J$_2$=1.1 1H 6Q), 6.86 (d, J=2.2 1H ar.), 6.67 (d, J-2.2 1H ar.), 5.32 (s, 2H-OCH$_2$Q), 3.6 (m, 2H), 2.79 (m, 2H), 2.74 (D, J=15.2 1H), 2.64 (d, J=14.2, 1H), 2.55 (m, 2H, 2.0 (q, J=7.2, 2H, CH$_2$CH$_3$), 1.22 (5, J=7.5 3H CH$_2$CH$_3$), 0.66 (t, J=7.2 3H, 8 CH$_2$CH$_3$).

IR: (KBr): 3400 (NH, OH), 1740 (C=O) cm$^{-1}$.

Mass: (M+−H), 445, 239, 217.

Analysis for: C$_{27}$H$_{28}$N$_2$O$_4$ Calculated: C, 72.95; H, 6.35; N, 6.30. Found: C, 71.04; H, 6.19; N, 6.21.

EXAMPLE 9

1-Ethyl-1,3,4,9-tetrahydro-6-(quinolinylmethoxy)-pyrano[3,4-b]indole-1-acetic acid A. 1-Ethyl-1,3,4,9-tetrahydro-6-(phenylmethoxy)-pyrano[3,4-b]indole-1-acetic acid methyl ester A mixture consisting of 5-benzyloxytryptophol (24.0 g, 0.090 mol), methylene chloride (600 mL), methyl 3-methoxy-2-pentenoate (16.8 g, 0.177 mol) and boron-trifluoride etherate (2 mL) is stirred at room temperature for 3 hours. The reaction mixture is washed with 5% $NaHCO_3$ (2×200 mL), water (2×200 mL) and once with brine (200 mL), dried ($MgSO_4$), filtered and concentrated to give 38.0 g crude product. The crude product is flash chromatographed on silica gel using 20% ethyl acetate/hexane as an eluent to afford 29.0 g pure title compound, m.p. 98°–100° C.

$^1$H NMR, $CDCl_3$): δ8.87 (BS, 1H NH), 7.47 (d, J=7.3, 2H Bz), 7.36 (t, J=7.6, 2H Bz), 7.29 (m, 1H), 7.24 (d, J=7.5, 1H), 7.04 (d, J=2.4, 1H), 6.91 (dd, $J_1$=8.7, $J_2$=2.4, 1H), 5.10 (s, 2H O—$CH_2$—Bz) 4.06–3.90 (m, 2H), 3.71 (s, 3H $CH_2COOCH_3$), 2.99 (d, J=16.6, 1H), 2.89 (d, J=16.6, 1H), 2.75 (m, 2H), 2.0 (m, 2H), 0.81 (t, J=7.4 3H $CH_2CH_3$).

Mass: (M+) 379, 350, 288.

Analysis for: $C_{23}H_{25}NO_4$ Calculated: C, 72.80; H, 6.64; N, 3.69. Found: C, 72.61; H, 6.63; N, 3.69.

B. 1-Ethyl-1,3,4,9-tetrahydro-6-(phenylmethoxy)-pyrano[3,4-b]indole-1-acetic acid A mixture consisting of the ester (29.0 g, 0.0765 mol) of Step A, methanol (800 mL), water (50 mL) and potassium hydroxide (16.0 g, 0.29 mol) is refluxed for 4 hours. The reaction mixture is cooled to room temperature, concentrated and diluted with water (500 mL). The aqueous layer is washed with ether (2×200 mL) and made acidic with a 1:1 mixture of concentrated HCl and water to pH 2.71 is extracted with chloroform (4×300 mL) and the combined chloroform layers are washed once with water (2×300 mL), once with brine (300 mL), dried ($MgSO_4$), filtered and concentrated to give 26.0 g of title compound, m.p. 163°–165° C.

$^1$H NMR (400 MHz, $CDCl_3$): δ8.39 (BS, NH), 7.47 (d, J=7.4, 2H), 7.38 (dt, $J_1$=7.1, $J_2$=1.8, 2H), 7.30 (m, 1H), 7.22 (d, J=8.7, 1H), 7.04 (d, J=2.4 1H), 6.90 (dd, $J_1$=8.8, $J_2$=2.4 1H), 5.10 (s—$OCH_2$ Bz) 4.08 (m, 2H), 3.02 (d, J=16.4 1H), 2.95 (d, J=16.3, 1H), 2.80 (q, J=5.0 2H), 2.06 (m, 2H), 0.86 (t, J=7.3 3H $CH_2CH_3$).

IR (KBr): 3380 (NH), 1710 (CO) $cm^{-1}$.

Mass: (M+) 365, ions 336, 306.

Analysis for: $C_{22}H_{23}NO_4$ Calculated: C, 72.31; H, 6.34; N, 3.83. Found: C, 72.17; H, 6.29; N, 3.65.

C. 1-Ethyl-1,3,4,9-tetrahydro-6-hydroxy-pyrano[3,4-b]indole-1-acetic acid

A mixture consisting of 10% Pd/c on charcoal (3.5 g), ethanol (800 mL), tetrahydrofuran (100 mL) and the acid (21.0 g, 0.056 mol) of Step B, is hydrogenated at 30 psi for 18 hours. The reaction mixture is filtered and concentrated to give 21.0 g of crude product, which is used in the next reaction without further purification.

$^1$H NMR (DMSO-$d_6$): δ10.36 (s, NH), 7.16 (d, J=7.4, 1H Ar), 6.68 (d, J=2.2 1H Ar), 6.53 (dd, $J_1$=8.5, $J_2$=2.2 1H Ar), 3.89 (m, 2H), 2.82 (d, J=13.6, 1H), 2.62 (d, J=13.6, 1H), 2.58 (m, 2H), 2.0–1.90 (m, 2H), 0.61 (t, J=7.3 3H $CH_2CH_3$).

IR (KBr): Broad peak. 3700–3300 $cm^{-1}$ (NH, OH), 1710 $cm^{-1}$ (C=O).

Mass: M ion: 275, ion 246, 216, 202.

Analysis for: $C_{15}H_{17}NO_4$ Calculated: C, 65.44; H, 6.22; N, 5.09. Found: C, 68.82; H, 6.72; N, 4.81.

D. 1-Ethyl-1,3,4,9-tetrahydro-6-(quinolinylmethoxy)-pyrano[3,4-b]indole-1-acetic acid A mixture consisting of the 6-hydroxy pyrano acid (21.0 g, 0.076 mol) of Step C, dimethyl sulfoxide (900 mL), sodium hydroxide (180.0 g in 100 mL $H_2O$) and 2-chloromethylquinoline hydrochloride (23.0 g, 0.0107 mol) is heated to 70°–80° C. for 1 hour. The reaction mixture is cooled, poured into water (1500 mL) and made acidic with 1N HCl to pH 4. It is extracted with ethyl acetate (4×500 mL) and the combined organic layers are washed once with water (2×300 mL), once with brine (300 mL), dried ($MgSO_4$), filtered and concentrated to give 33.0 crude product, which is chromatographed on silica gel using 7% methanol/methylene chloride as eluent to afford 13.9 g pure product. The pure product is dissolved in 100 mL ethyl acetate, and precipitated by adding dropwise to petroleum ether (3000 mL), and filtered to give 13.8 g product, which is crystallized from benzene to give 12.0 g of pure product, m.p. 105° C. (dec.).

$^1$H NMR DMSO-$d_6$: δ10.59 (s, 1H, NH), 8.39 (d, J=8.5, 1H, 4Q), 8.01 (d, J=8.5, 1H, 8Q), 7.97 (d, J=8.2, 1H, 5Q), 7.78 (dt, $J_1$=6.9, $J_2$=1.4, 1H 7Q), 7.70 (d, J=8.5, 1H, 3Q), 7.60 (dt, $J_1$=6.9, $J_2$=1.0, 1H, 6Q), 7.21 (d, J=8.7, 1H ar.), 7.06 (d, J=22.3, 1H Ar), 6.82 (dd, $J_1$=8.7, $J_2$=2.5, 1H Ar.), 5.34 (s, 2H, O—$CH_2$—Q), 3.92–3.86 (m, 2H), 2.82 (d, J=13.6, 1H), 2.62 (d, J=18.6, 1H), 2.60 (m, 2H), 2.01–1.91 (m, 2H), 0.61 (t, J=7.3, $CH_2CH_3$).

IR (KBr): 3400 $cm^{-1}$ (NH,OH) 1705 $cm^{-1}$ (C=O).

Mass: FAB: M+H 417 ion M+ 357.

Analysis for: $C_{25}H_{25}N_2O_4$ Calculated: C, 72.10; H, 5.81; N, 6.73. Found: C, 72.55; H, 5.91; N, 6.48.

EXAMPLE 10

1-Methyl-1,3,4,9-tetrahydro-6-(2-quinolinylmethoxy)-pyrano[3,4-b]indole-1-acetic acid A. 1-Methyl-1,3,4,9-tetrahydro-6-(phenylmethoxy)-pyrano[3,4-b]indole-1-acetic acid, ethyl ester A mixture consisting of 5-benzyloxytryptophol (4.5 g, 0.017 mol), benzene (200 mL), ethyl acetoacetate (3.4 g, 0.026 mol) and p-toluenesulfonic acid (0.5 g) is refluxed for 2.5 hours using a Dean-stock trap to remove the water. The reaction mixture is cooled to room temperature and washed with 5% sodium bicarbonate, (1×200 mL), water (200 mL) and brine (100 mL), dried ($MgSO_4$), filtered and concentrated to give 8.0 g of crude product as a thick oil, which is flash chromatographed on silica gel using 20% ethyl acetate/hexane as an eluent to afford 5.5 g oil which solidifies upon standing, m.p. 96°–98° C.

$^1$H NMR 400 MHz $CDCl_3$: δ8.96 (bs, 1H, NH), 7.47 (d, J=7.0, 2H ar., O—Bz), 7.36 (dt, $J_1$=7.1, $J_2$=1.8, 2H Ar., O—$CH_2Bz$), 7.3 (m, 1H, $OCH_2$—Bz), 7.23 (d, J=8.7 1H Ar.), 7.04 (d, J=2.5, 1H Ar.), 6.90 (dd, $J_1$=8.7, $J_2$=2.3 1H Ar), 5.10 (s, 2H, O—$CH_2$—φ), 4.22–4.14 (m, 2H), 4.01 (m, 2H), 2.98 (d, J=16.5, 1H), 2.85 (d, J=16.4, 1H), 2.79 (t, J=2H), 1.7 (s, 3H, $CH_2$), 1.3 (t, J=3H $COOCH_2CH_3$).

Mass: EI: M/e: 379, ions 292, 158.

B. 1-Methyl-1,3,4,9-tetrahydro-6-(phenylmethoxy)-pyrano[3,4-b]indole-1-acetic acid A mixture consisting of the ester (5.5 g, 0.013 mol) of Step A., methanol (300 mL), water (20 mL) and potassium hydroxide (4.0 g, 0.071 mol) is refluxed for 4 hours.

The reaction mixture is cooled to room temperature, concentrated, diluted with water (200 mL) and made acidic with 1:1 solution of concentrated HCl:water to pH of 1. The mixture is extracted with chloroform (3×150 mL), the combined chloroform extracts are washed once with water (2×100 mL), once with brine (100 mL), dried (MgSO$_4$), filtered and concentrated to give 4.6 g of product, which is used in the next reaction, m.p. 157°–158° C. (dec.).

$^1$H NMR (400 MHz, DMSO-d$_6$): δ11.98 (bs, 1H, COOH), 10.62 (s, 1H, NH), 7.45 (d, J=7.1, 2H—Bz), 7.38 (dt, J$_1$=7.1, J$_2$=1.8, 2H, BzO, 7.30 (m, 1H, Bz), 7.18 (d, J=8.7, 1H Ar.), 6.99 (d, J=2.3, 1H Ar.), 6.76 (dd, J$_1$=8.7, J$_2$=2.5, 1H Ar.), 5.07 (s, 2H, OCH$_2$φ), 3.95–3.84 (m, 2H), 2.78 (d, J=13.8, 1H), 2.68 (d, J=13.8, 1H), 2.60 (t, J=5.4, 2H), 1.56 (s, 3H).

Mass: EI: M/e: 351, ions 292, 260, 130.

C. 1-Methyl-1,3,4,9-tetrahydro-6-hydroxypyrano[3,4-b]indole-1-acetic acid

A mixture consisting of the acid (4.5 g, 0.013 mol) of Step B, ethanol (150 mL), tetrahydrofuran (20 mL) and 10% Pd/c on charcoal (800 mg) is hydrpgenated at 30 psi for 18 hours. The mixture is filtered and concentrated to give 3.1 g of product, which is used into next reaction without further purification.

$^1$H NMR (400 MHz, DMSO-d$_6$): δ7.19 (d, J=8.5, 1H Ar.), 6.70 (d, J=2.5, 1H Ar.), 6.55 (dd, J$_1$=8.5, J$_2$=2.5, 1H Ar.), 3.90 (m, 2H), 2.77 (d, J$_1$=16.0, 1H), 2.66 (d, J=16.0, 1H), 2.55 (m, 2H), 1.55 (s, 3H).

Mass: EI: M/e: 261, ions: 216, 160, 101.

D. 1-Methyl-1,3,4,9-tetrahydro-6-(2-quinolinylmethoxy)pyrano[3,4-b]indole-1-acetic acid A mixture consisting of 1-methyl-1,3,4,9-tetrahydro-6-hydroxypyrano[3,4-b]indole-1-acetic acid (3.0 g, 0.011 mol) of Step C, dimethyl sulfoxide (300 mL), potassium iodide (100 mg) and sodium hydroxide (2.5 g in 20 mL water) is stirred at room temperature. 2-Chloromethylquinoline hydrochloride (5.8 g, 0.022 mol) is added and the reaction mixture is heated for 3.5 hours, cooled and diluted with water (700 mL). The mixture is made acidic to pH 4 with 1N HCl, extracted with ethyl acetate (4×300 mL) and the combined organic layers are washed once with water (2×200 mL), once with brine (200 mL), dried (MgSO$_4$), filtered and concentrated to yield crude product, which is flash chromatographed on silica gel using 10% methanol/methylene chloride as an eluent to give 1.0 g product. The latter is dissolved in ethyl acetate (20 mL) and precipitated by adding dropwise to petroleum ether (500 mL) to give 1.0 g pure compound, m.p. 175°–177° C. (dec.).

$^1$H NMR (400 MHz DMSO-d$_6$): δ11.2 (bs, 1H, NH), 8.37 (d, J=8.5, 1H 4Q), 8.0 (d, J=8.7 1H, 8Q), 7.97 (d, J=7.6, 1H, 5Q), 7.77 (dt, J$_1$=6.9, J$_2$=1.4, 1H, 7Q), 7.69 (d, J=8.5, 1H, 3Q), 7.58 (dt, J$_1$=7.0, J$_2$=1.0, 1H, 6Q), 7.18 (d, J=8.7, 1H Ar.), 7.03 (d, J=2.3 1H Ar.), 6.80 (dd, J$_1$=8.7, J$_2$=2.3 1H Ar), 5.34 (s, 2H, OCH$_2$Q), 3.88–3.84 (m, 2H), 2.62 (bs, 2H), 2.48 (bs, 2H), 1.56 (s, 3H—CH$_3$).

IR (KBr): 3400 cm$^{-1}$ (broad NH, OH,), 1700 cm$^{-1}$ (C=O).

Mass: EI: M/e: M+ 402, ions 202, 157.

Analysis for: C$_{24}$H$_{22}$N$_2$O$_4$ Calculated: C, 71.63; H, 5.57; N, 6.96. Found: C, 69.20; H, 5.38; N, 6.60.

EXAMPLE 11

1-Ethyl-2,3,4,9-tetrahydro-6-(2-quinolinylmethoxy)-1H-carbazole-1-acetic acid

A. 1-Ethyl-2,3,4,9-tetrahydro-6-methoxy-1H-carbazole-1-acetic acid methyl ester

A mixture consisting of 4-methoxyphenylhydrazine (25.0 g, 0.162 mol), 2-carbomethoxymethyl-2-ethylcyclohexanone (42.0 g, 0.212 mol), and toluene (1000 mL) is refluxed for 24 hours under a nitrogen atmosphere and the water is removed using a Dean-Stark trap. The reaction mixture is cooled and concentrated to give crude hydrazone. (≈56 g).

The crude hydrazone (56 g) is dissolved in glacial acetic acid (500 mL) and refluxed for 25 minutes. The reaction mixture is cooled to room temperature, poured into water (2000 mL) and extracted with ethyl acetate (4×500 mL). The organic layers are combined, washed with 1N NaOH (2×500 mL), water (2×500 mL), once with brine (500 mL), dried (MgSO$_4$), filtered and concentrated to give 47.0 g of crude product. The crude product is flash chromatographed using 10% ethyl acetate/hexane as an eluent to afford 18.0 g product; m.p. 72°–74° C.

$^1$H NMR (400 MHz, CDCl$_3$): δ8.94 (bs, 1H, NH), 7.19 (d, J=8.0, 1H Ar.), 6.90 (d, J=2.3 1H Ar.), 6.76 (dd, J$_1$=8.6, J$_2$=2.3, 1H Ar.), 3.81 (s, 3H, COOCH$_3$), 3.64 (s, 3H, OCH$_3$), 2.68–2.62 (m, 4H), 1.95–1.61 (m, 6H), 0.8 (t, J$_1$=7.6, 3H, CH$_2$CH$_3$).

Mass: EI: M/e: 301, ions 272, 228 (base peak).

B. 1-Ethyl-2,3,4,9-tetrahydro-6-hydroxy-1H-carbazole-1-acetic acid

A mixture consisting of the methoxy compound (18.0 g, 0.060 mol) of Step A, and 48% hydrobromic acid (450 mL) is heated at 125° C. for 6 hours. The reaction mixture is cooled, diluted with water (1500 mL) and extracted with ethyl acetate (3×500 mL). The organic layers are combined and washed once with water (2×500 mL), once with brine (500 mL), dried (MgSO$_4$), filtered and concentrated to give 15.8 g product as a foam.

$^1$H NMR (400 MHz, DMSO-d$_6$): δ10.21 (s, 1H, COOH), 8.45 (bs, 1H, NH), 7.03 (d, J=8.5, 1H Ar.), 6.63 (d, J=1.9, 1H, Ar.), 6.48 (dd, J$_1$=7.3, J$_2$=1.3, 1H Ar.), 2.54–2.46 (m, 4H), 1.98–1.66 (m, 6H), 0.70 (t, J=7.3, CH$_2$CH$_3$).

Mass: EI: M/e: 273 (M+) ions 244, 214, 198.

C. 1-Ethyl-2,3,4,9-tetrahydro-6-(2-quinolinylmethoxy)-1H-carbazole-1-acetic acid A mixture consisting of the hydroxy acid (8.0 g, 0.028 mol) of Step B, dimethyl sulfoxide (500 mL), potassium iodide (100 mg), and sodium hydroxide (7.0 g in 300 mL H$_2$O 0.175 mol) is stirred at room temperature, for 15 minutes. 2-Chloromethylquinoline hydrochloride (11.8 g, 0.055 mol) is added and the reaction mixture is heated to 70°–80° C. for 3 hours. The mixture is cooled to room temperature and poured into water (1500 mL), made acidic to pH 4 with 1N HCl, and extracted with ethyl acetate (3×500 mL). The organic layers are combined, washed once with water (2×300 mL), once with brine (300 mL). The organic layers are combined, washed once with water (2×300 mL), once with brine (300 mL), dried (MgSO$_4$), filtered and concentrated to give 9.0 g of crude product which is flash chromatographed using 10% methanol/methylene chloride as an eluent to give 3.0 g pure product, which is dissolved in ethyl acetate (20 mL) and added dropwise to petroleum ether (500 mL). The precipitate is filtered off to give 2.5 g product, m.p. 120°-125° C.

¹H NMR (400 MHz, DMSO-d₆): δ10.80 (bs, 1H, NH), 8.37 (d, J=8.5, 1H, 4Q), 8.0 (d, J=8.5, 1H, 8Q), 7.98 (d, J=7.2, 1H 5Q), 7.77 (dt, J₁=6.9, J₂=1.5, 1H, 7Q), 7,69 (d, J=8.5, 1H, 3Q), 7.61 (dt, J₁=6.9, J₂=1.1, 1H, 6Q), 7.14 (d, J=8.7, 1H Ar.), 6.96 (d, J=2.4, 1H Ar.), 6.76 (dd, J₁=8.6, J₂=2.4, 1H Ar.), 5.32 (s, 2H —CH₂Q), 2.52 (bs, 2H), 1.82-1.72 (m, 8H), 0.71 (t, J=7.3, 3H, CH₂CH₃).

IR (KBr): 3410 cm⁻¹ (NH, OH, broad), 1710 cm⁻¹ (C=O).

Mass: M⁺ 415

Analysis for: C₂₆H₂₆N₂O₃ Calculated: C, 75.34; H, 6.32; N, 6.76. Found: C, 73.49; H, 6.27; N, 6.48.

EXAMPLE 12

1,3,4,9-Tetrahydro-1-propyl-6-(2-quinolinylmethoxy)-pyrano[3,4-b]indole-1-acetic acid A. Ethyl-1-propyl-1,3,4,9-tetrahydro-6-(phenylmethoxy)pyrano[3,4-b]indole-1-acetate A solution of 5-benzyloxytryptophol (4.72 g, 17 mmol) and ethyl butyrylacetate (3.16 g, 20 mmol) in methylene chloride (75 ml) is treated dropwise with boron trifluoride etherate (3 mL) and stirred under nitrogen at room temperature overnight. The reaction mixture is diluted with methylene chloride (250 mL) and sequentially washed with 5% aqueous sodium bicarbonate (2×100 mL) and water (2×50 mL). The organic phase is dried (MgSO₄), filtered, and evaporated to afford 7.0 g of a crude dark oil. Purification by flash column chromatography (ethyl acetate:hexane, 1:9 eluent) on silica gel (50:1 ratio, 230-400 mesh) affords the title compound (5.5 g, 79%) as a slightly amber oil homogeneous by TLC.

¹H NMR (200 MHz, CDCl₃): δ8.93 (bs, 1H, NH), 7.25-7.80 (m, 5H, C₆H₅), 7.22 (d, J=9.3 Hz, 1H, 8-ArH), 7.04 (d, J=2.8 Hz, 1H, 5-ArH), 6.91 (dd, J=9.3, 2.8 Hz, 1H, 7-ArH), 5.12 (s, 2H, OCH₂Ar), 3.83-4.40 (m, 4H, CH₂ ester, 3-H's), 3.03, 2.86 (d, J=17.2 Hz, 2H, CH₂CO₂C₂H₅), 2.60-2.87 (m, 2H, 4-H's), 1.82-2.20 (m, 2H, 1-CH₂(α)), 1.25 (t, J=7.0 Hz, 3H, CH₃ ester), 1.00-1.50 (m, 2H, 1-CH₂(β)), 0.86 (t, J=7.0 Hz, 3H, 1-CH₃).

B. Ethyl-1-propyl-1,3,4,9-tetrahydro-6-hydroxypyrano[3,4-b]indole-1-acetate

A suspension of the 6-benzyloxypyranoindole (5.4 g, 13.25 mmol) of Step A, and 10% Pd/C catalyst (600 mg) in ethanol (150 mL) is hydrogenated for 6 hours in a Parr shaker. Filtration of the catalyst and evaporation of the solvent affords the title compound (3.75 g, 89%) as a cream-colored foam homogeneous by TLC.

¹H NMR (200 MHz, CDCl₃); δ8.90 (bs, 1H, NH), 7.20 (d, J=9.3 Hz, 1H, 8-ArH), 6.92 (d, J=2.8 Hz, 1H, 5-ArH), 6.75 (dd, J=9.3, 2.8 Hz, 1H, 7-ArH), 4.90 (bs, 1H, OH), 3.85-4.40 (m, 4H, CH₂ ester, 3-H's), 3.02, 2.88 (d, J=17.2 Hz, 2H, CH₂CO₂C₂H₅), 2.57-2.88 (m, 2H, 4-H's), 1.82-2.20 (m, 2H, 1-CH₂(α)), 1.25 (t, J=7.0 Hz, 3H, CH₃ ester), 1.00-1.60 (m, 2H, 1-CH₂(β)), 0.87 (t, J=7.0 Hz, 3H, 1-CH₃).

C. 1,3,4,9-Tetrahydro-1-propyl-6-(2-quinolinylmethoxy)pyrano[3,4-b]indole-1-acetic acid A solution of the 6-hydroxypyranoindole (3.5 g, 11 mmol) of Step B, in dimethylsulfoxide (80 mL) is treated with 2.5N NaOH (20 mL, 50 mmol) and stirred at 40° C. under nitrogen for 5 minutes. 2-Chloromethylquinoline hydrochloride (4.71 g, 22 mmol) is added as a solid in one aliquot and the reaction mixture heated to 80° C. for 30 minutes. After cooling, the pH of the reaction is adjusted to 12.0 with 2.5N NaOH. After extraction with ether (3×250 mL), the aqueous layer is carefully acidified to pH 3.0 with 2N HCl and 0.1N HCl (near end point) followed by rapid extraction with ether (4×300 mL). The combined ether extracts are washed with water (2×200 mL), dried (MgSO₄), and filtered. Evaporation of the solvent affords a crude yellow foam (4.16 g, 88%). Purification by flash column chromatography (methanol:methylene chloride, 5:95 eluent) on silica gel (100:1 ratio, 230-400 mesh) affords an amber foam (2.08 g, 61%) homogeneous by TLC. A concentrated methylene chloride solution of the foam is added dropwise to cooled, rapidly stirred, petroleum ether (200 mL). Filtration of the resulting precipitate yields the title compound as a cream colored amorphous solid (3.2 g, 61%) homogeneous by TLC. After high vacuum drying (36 hours) the compound still retains solvent of crystallization as indicated by NMR, m.p. 100°-110° C. (dec.).

IR (KBr): 3400 (NH, OH), 1710 (C=O) cm⁻¹.

¹H NMR (400 MHz, CDCl₃): δ8.93 (s, 1H, NH), 8.26 (d, J=8.5 Hz, 1H, 4-Q), 8.19 (d, J=8.6 Hz, 1H, 8-Q), 7.85 (d, J=8.2 Hz, 1H, 5-Q), 7.81 (d, J=8.5 Hz, 1H, 3-Q), 7.76 (dt, J=7.0, 1.2 Hz, 1H, 7-Q), 7.58 (t, J=7.0 Hz, 1H, 6-Q), 7.07 (d, J=2.4 Hz, 1H, 5-ArH), 6.97 (d, J=8.8 Hz, 1H, 8-ArH), 6.84 (d, J=8.8, 2.4 Hz, 1H, 7-ArH), 5.49 (s, 2H, OCH₂Q), 4.03 (ddd, J=11.4, 4.7, 4.3 Hz, 1H, 3-Heq.), 3.92 (ddd, J=11.4, 7.2, 4.8 Hz, 1H, 3- - - Hax), 3.05 (d, J=16.8 Hz, 1H, 4-Hax), 2.66 (ddd, J=15.4, 4.7, 4.7 Hz, 1H, 4-Heq.), 1.91-2.14 (m, 2H, 1-CH₂(α)), 1.08-1.48 (m, 2H, 1-CH₂(β)), 0.88 (t, J=7.0 Hz, 3H, 1-CH₃).

MS (EI); m/e 430 (1.4, M⁺), 160 (50, QCH₂OH₂⊕), 143 (100, QCH₃⊕).

Analysis for: C₂₆H₂₆N₂O₄Calculated: C, 72.54; H, 6.09; N, 6.51. Found: C, 72.64; H, 7.52; N, 5.41.

EXAMPLE 13

1-Ethyl-1,3,4,9-tetrahydro-6-(2-quinolinylmethoxy)-pyrano[3,4-b]indole-1-acetic acid, methyl ester Trimethylsilyldiazomethane (40 mL, 10% by weight methylene chloride) is added dropwise to a mixture consisting of 1-ethyl-1,3,4,9-tetrahydro-(2-quinolinylmethoxy)pyrano[3,4-b]indole-1-acetic acid (1.0 g, 0.002 mol) as prepared in Example 9, methylene chloride (150 mL) and methanol (15 mL). The reaction mixture is stirred at room temperature for ½ hour, and is concentrated to give 1.2 g of oily residue, which is very difficult to crystallize. The ester is converted to the hydrochloride salt by adding ether/HCl. The hydrochloride salt is recrystallized from methanol/ether to afford 0.75 g pure compound, m.p. 185°-187° C.

¹H NMR (400 MHz, DMSO-d₆): δ8.71 (d, J=8.2 Hz, 1H, 4Q), 8.21 (d, J=8.2 Hz, 1H, 8Q), 8.13 (d, J=8.2 Hz, 1H, 5Q), 7.93-7.89 (m, 2H, 3Q, 7Q), 7.76 (t, J=7.8 Hz, 6Q), 7.23 (d, J=8.6 Hz, 1H Ar), 7.10 (d, J=2.6 Hz, 1H Ar), 6.86 (dd, J₁=8.6, J₂=2.3, 1H Ar.), 5.5 (s, 2H, OCH₂-q), 3.91 (m, 2H), 3.51 (s, 3H, COOCH₃), 2.91 (d, J=13.7 Hz, 1H), 2.74 (d, J=13.5 Hz, 1H), 2.56 (m, 2H), 1.93 (q, J=7.4 Hz, 2H), 0.60 (t, J=7.2 Hz, 3H, CH₂CH₃).

IR (KBr) 3400 cm⁻¹, 3200 cm⁻¹ (NH, OH), 1740 cm⁻¹ (C=O).

Mass: EI (m/e) M⁺ 430, ions 401, 357.

Analysis for: C₂₆H₂₆N₂O₄.HCl Calculated: C, 66.88; H, 5.83; N, 6.00. Found: C, 66.58; H, 5.75; N, 5.96.

EXAMPLE 14

1,3,4,9-Tetrahydro-1,1-dimethyl-6-(2-quinolinylmethoxy)pyrano[3,4-b]indole

A. 1,3,4,9-Tetrahydro-1,1-dimethyl-6-(phenylmethoxy)pyrano[3,4-b]indole

A mixture consisting of 5-benzyloxytryptophol (3.2 g, 0.012 mol), acetone (7 mL), benzene (300 mL) and p-toluene sulfonic acid (500 mg) is refluxed for 3.5 hours using a Dean-Stark trap to remove the water. The reaction mixture is cooled to room temperature and washed with 5% sodium bicarbonate (1×200 mL), water (200 mL) and brine (200 mL). It is dried (MgSO$_4$), filtered and concentrated to give 5.0 g product as thick oil. The crude product is flash chromatographed with 15% ethyl acetate/hexane as an eluent to afford 2.5 g product, m.p. 128°–129° C.

B. 1,3,4,9-Tetrahydro-1,1-dimethyl-6-hydroxypyrano[3,4-b]indole

A mixture consisting of 10% Pd/c on charcoal (0.7 g), ethanol (150 mL) and 1,3,4,9-tetrahydro-1,1-dimethyl-6-(phenylmethoxy)pyrano[3,4-b]indole (4.2 g, 0.014 mol) of Step A, is hydrogenated at 30 psi for 18 hours. The reaction mixture is filtered and concentrated to give 3.5 g product which is used in the next reaction without further purification.

C. 1,3,4,9-Tetrahydro-1,1-dimethyl-6-(2-quinolinylmethoxy)pyrano[3,4-b]indole

A mixture consisting of the 6-hydroxy compound (3.5 g, 0.016 mol) of Step B, dimethylformamide (100 mL), potassium carbonate, anhydrous (6.0 g, 0.043 mol), potassium iodide (100 mg) and 2-chloromethylquinoline (2.9 g, 0.016 mol) is heated at 60° C. for 24 hours. The reaction mixture is cooled to room temperature, diluted with water (600 mL), and extracted with ethyl acetate (3×150 mL). The combined organic layers are washed with 2.5N NaOH, water (2×100 mL), once with brine (100 mL), dried (MgSO$_4$) and concentrated to give 3.8 g of crude product. The crude product is flash chromatographed on silica gel using 40% ethyl acetate/hexane as an eluent to afford 2.3 g of product which is recrystallized from methanol to afford 1.69 g pure title compound, m.p. 164°–165° C.

$^1$H NMR (400 MHz, DMSO-d$_6$): δ10.68 (s, 1H, NH), 8.38 (d, J=8.6 Hz, 1H, 4Q), 8.0 (d, J=8.4 Hz, 1H, 8Q), 7.97 (d, J=8.1 Hz, 1H, 5Q), 7.77 (t, J=7.1 Hz, 1H, 7Q), 7.69 (d, J=8.6 Hz, 1H, 3Q), 7.59 (t, J=7.1 Hz, 1H, 6Q), 7.18 (d, J=8.7 Hz, 1H Ar), 7.04 (d, J=2.4 Hz, 1H Ar), 6.82 (dd, J$_1$=8.6, J$_2$=2.4 Hz, 1H Ar), 5.34 (s, 2H, OCH$_2$Q), 3.85 (t, J=5.3 Hz, 2H), 2.56 (t, J=5.3 Hz, 2H), 1.44 (s, 6H, (CH$_3$)$_2$).

IR (KBr): 3410 cm$^-$ (broad NH).

Mass: EI: m/e: 358 (M+) 343 143.

Analysis for: C$_{23}$H$_{22}$N$_2$O$_2$ Calculated: C, 77.07; H, 6.19; N, 7.81. Found: C, 76.76; H, 6.25; N, 7.70.

EXAMPLE 15

1,3,4,9-Tetrahydro-1,1-diethyl-6-(2-quinolinylmethoxy)pyrano[3,4-b]indole

A. 1,3,4,9-Tetrahydro-1,1-diethyl-6-(phenylmethoxy)pyrano[3,4-b]indole

A mixture consisting of 5-benzyloxytryptophol (7.0 g, 0.0262 mol), diethyl ketone (10 mL), benzene (400 mL) and p-toluene sulfonic acid is refluxed for 3.5 hours using a Dean-Stark tap to remove the water. The reaction mixture is cooled to room temperature, washed with 5% sodium bicarbonate, water (200 mL), brine (200 mL), dried (MgSO$_4$), filtered and concentrated to give 9.9 g of crude product. The crude product is flash chromatographed on silica gel using 15% ethyl acetate/hexane as an eluent to afford 6.5 g of pure title compound.

B. 1,3,4,9-Tetrahydro-1,1-diethyl-6-(hydroxy)pyrano[3,4-b]indole

A mixture consisting of 10% Pd/c on charcoal (1.0 g), ethanol (125 mL), and 1,3,4,9-tetrahydro-1,1-diethyl-6-(phenylmethoxy)pyrano[3,4-b]indole (6.5 g, 0.0193 mol), of Step A, is hydrogenated at 30 psi for 18 hours. The reaction mixture is filtered and concentrated to give 5.2 g of product which is used in the next reaction without further purification.

C. 1,3,4,9-Tetrahydro-1,1-diethyl-6-(2-quinolinylmethoxy)pyrano[3,4-b]indole

A mixture consisting of the 6-hydroxy compound (5.2 g, 0.0212 mol) of Step B, dimethyl sulfoxide (150 mL), sodium hydroxide (6.0 g, 0.15 mol in 20 mL water), and 2-chloromethylquinoline hydrochloride (6.0 g, 0.028 mol) is heated to 70°–80° C. for 6 hours. The reaction mixture is cooled to room temperature, diluted with water (800 mL), and extracted with ethyl acetate (3×150 mL). The combined organic layers are washed once with water (2×150 mL), once with brine (100 mL), dried (MgSO$_4$), filtered and concentrated to give 9.9 crude product. The crude product is flash chromatographed on silica gel using 25% ethyl acetate/hexane as an eluent to afford 4.5 g pure product as a thick oil. The oil is dissolved in ether (150 mL) and ether/HCl is added dropwise. The precipitate is filtered off and the product crystallized from methanol/ether to give 2.6 g product as a yellow crystalline solid, m.p. 164°–166° C.

$^1$H NMR (400 MHz, DMSO-d$_6$): δ10.64 (s, 1H, NH), 8.70 (d, J=8.6 Hz, 1H, 4Q), 8.21 (d, J=8.5 Hz, 1H, 8Q), 8.13 (d, J=8.1 Hz, 1H, 5Q), 7.95–7.88 (m, 2H, 3 and 7Q), 7.74 (t, J=7.3 Hz, 1H, 6Q), 7.21 (d, J=8.6 Hz, 1H Ar), 7.08 (d, J=2.4 Hz, 1H Ar), 6.84 (dd, J$_1$=8.7, J$_2$=2.4 Hz, 1H Ar.), 5.50 (s, 2H, OCH$_2$Q), 3.85 (t, J=5.3 Hz, 2H), 2.57 (t, J=5.4 Hz, 2H), 1.80 (m, 4H, CH$_2$CH$_3$1,1-diethyl), 0.71 (t, J=7.3 Hz, 6H, CH$_2$CH$_3$, 1,1-diethyl).

IR: (KBr) 3410 cm$^{-1}$ (NH).

Mass: EI: M/e: 386 (M+) ions 357, 216, 142, 128.

Analysis for: C$_{25}$H$_{26}$N$_2$O$_2$.HCl Calculated: C, 70.99; H, 6.43; N, 6.62 Found: C, 71.20; H, 6.43; N, 6.66.

EXAMPLE 16

1-[(4-Chlorophenyl)methyl]-2-methyl-5-(2-quinolinylmethoxy)-1H-indole-3-acetic acid hydrochloride quarter hydrate A. 2-Methyl-5-(2-quinolinylmethoxy)-1H-indole-3-acetic acid, one tenth hydrate To a previously degassed mixture of dimethylformamide (70 mL) and sodium methoxide/methanol solution (25 wt %, 2 equivalents, 8.8 mL) is added 5-hydroxy-2-methyl-1H-indole-3-acetic acid (4.0 g, 19.5 mmol) at room temperature. After 15 minutes 2-chloromethylquinoline (3.46 g, 19.5 mmol) is added and the mixture stirred overnight. The dimethylformamide is evaporated and the mixture partitioned between pH 4 buffer solution and ethyl acetate. The organic phase is dried (MgSO$_4$), filtered and partially concentrated. A solid is filtered off and crystallized using ethanol-water. This gives the title compound as a solid (2.96 g), 44% yield, m.p. 208°–210° C.

Analysis for: $C_{21}H_{18}N_2O_3 \cdot 0.1\ H_2O$ Calculated: C, 72.44; H, 5.26; N, 8.04. Found: C, 72.29; H, 5.38; N, 7.93.

B. 2-Methyl-5-(2-quinolinylmethoxy)-1H-indole-3-acetic acid methyl ester.

To a stirring mixture of the indole-acetic acid substrate (1.2 g, 3.4 mmol) in tetrahydrofuran (25 mL) is added slowly, a freshly prepared diazomethane/diethyl ether solution at ambient temperature. Upon consumption of starting material, a few drops of acetic acid are added. The solvent is evaporated and methylene chloride is added. This organic phase is washed with water and dried ($MgSO_4$). Solvent removal gives the product as an oil (1.2 g). Yield is quantitative.

C. 1-[(4-Chlorophenyl)methyl]-2-methyl-5-(2-quinolinylmethoxy)-1-H-indole-3-acetic acid methyl ester To a stirring mixture of the indole-ester substrate (0.8 g, 2.2 mmol) in dimethylformamide (15 mL) is added sodium hydride (0.058 g, 2.4 mmol). The reaction is stirred for 30 minutes at ambient temperature. 4-Chlorobenzylchloride (0.35 g, 2.2 mmol) is then added. After 2 hours the dimethylformamide is evaporated and the residue partitioned using pH 4 buffer solution and ethyl acetate. The organic phase is separated, dried ($MgSO_4$) and filtered. Solvent removal produces a solid that is flash chromatographed using chloroform as eluent, then crystallized with acetonitrile to yield the product as a crystalline solid (0.162 g 16% yield) m.p. 132°-134° C.

Analysis for: $C_{29}H_{25}N_2O_3Cl$ Calculated: C, 71.82; H, 5.20; N, 5.78. Found: C, 71.48; H, 5.17; N, 5.88.

D. 1-[(4-Chlorophenyl)methyl]-2-methyl-5-(2-quinolinylmethoxy)-1H-indole-3-acetic acid hydrochloride quarter hydrate The above ester (2.2 g, 4.5 mmol) is combined with tetrahydrofuran (50 mL), 1N NaOH solution (50 mL) and heated to reflux (3.5 hours). The tetrahydrofuran is removed in vacuo and the aqueous phase acidified with 1N HCl. A crude solid is filtered and recrystallized using ethanol to produce 1.16 g of product as the hydrochloride salt (50% yield), m.p. 249°-251° C.

Analysis for: $C_{28}H_{23}ClN_2O_3 \cdot HCL \cdot \frac{1}{4}H_2O$ Calculated: C, 65.69; H, 4.82; N, 5.47. Found: C, 65.64; H, 4.92; N, 5.41.

EXAMPLE 17

1-(4-Chlorobenzoyl)-2-methyl-5-(2-quinolinylmethoxy)-1H-indole-3-acetic acid three quarters hydrate A. 1-(4-Chlorobenzoyl)-2-methyl-5-(2-quinolinylmethoxy)-1H-indole-3-acetic acid methyl ester one tenth hydrate To a solution of 2-methyl-5-(2-quinolinylmethoxy)-1H-indole-3-acetic acid methylester (0.95 g, 2.6 mmol) (see Example 16B) in dimethylformamide (10 mL) at 0° C. is added sodium hydride (0.12 g, 50% dispersion) and the mixture stirred 20 minutes. 4-Chlorobenzoyl chloride (0.45 g, 2.6 mmol) is then added and the mixture stirred overnight; 100 mL of 5% acetic acid is used to quench the reaction. After extraction with a 1:1 mixture of ether:ethyl acetate, the organic phase is washed with water, saturated $NaHCO_3$ solution, water and brine. It is then separated and dried ($MgSO_4$). Solvent removal gives a crude solid which is flash chromatographed using methylene chloride-methanol (99-1) as eluent. The product is isolated and crystallized from acetonitrile (0.20 g, m.p. 117°-118° C.), yield is 15%.

Analysis for: $C_{29}H_{23}ClN_2O_4 \cdot 0.1\ H_2O$ Calculated: C, 69.55; H, 4.66; N, 5.59. Found: C, 69.35; H, 4.48; N, 5.56.

B. 1-(4-Chlorobenzoyl)-2-methyl-5-(2-quinolinylmethoxy)-1H-indole-3-acetic acid three quarters hydrate To a mixture of the above ester (0.5 g, 1.0 mmol) in acetonitrile (20 mL) is added iodotrimethyl silane (0.46 g, 2.2 mmol). After refluxing for 24 hours the mixture is diluted with ethyl acetate then washed with 10% $Na_2S_2O_3$ solution, water and 15% $NaHCO_3$ solution. A precipitate forms which is filtered off, washed with 1N HCl and dried in vacuo to give the title compound as a solid (0.05 g, 10% yield), m.p. 191°-193° C.

Analysis for: $C_{28}H_{21}ClN_2O_4 \cdot 0.75\ H_2O$ Calculated: C, 67.47; H, 4.55; N, 5.62. Found: C, 67.68; H, 4.22; N, 5.94.

EXAMPLE 18

2-Methyl-5-(2-quinolinylmethoxy)-1,2-(quinolinylmethyl)-1H-indole-3-acetic acid

To a stirred suspension of sodium hydride (1.4 g, 29.2 mmol) in dimethylformamide (40 mL) at 0° C. is added 5-hydroxy-2-methyl-1H-indole-3-acetic acid (2.0 g, 9.76 mmol). After 1 hour 2-chloromethylquinoline (3.44 g, 19.48 mmol) is added and the reaction mixture is allowed to warm to room temperature. After stirring overnight water is added and the pH was adjusted to 5 with 0.5N HCl. The reaction mixture is extracted with methylene chloride, the organic extract is dried over $MgSO_4$ and evaporated to a solid which upon sequential trituration with ethanol and hot ethanol affords 2.5 g (52%) of a beige solid, m.p. 198°-200° C.

Analysis for: $C_{31}H_{25}N_3O_3$ Calculated: C, 76.37; H, 5.17; N, 8.62. Found: C, 76.72; H, 5.24; N, 8.74.

EXAMPLE 19

1-[(4-Chlorophenyl)methyl]-5-(hexyloxy)-2-methyl-1H-indole-3-acetic acid

A. 5-(Hexyloxy)-2-methyl-1H-indole-3-acetic acid

To a solution of 5-hydroxy-2-methyl-1H-indole-3-acetic acid (7.17 g, 35.0 mmol) in methanol (40 mL) is added sodium methoxide (70 mmol). The solution is evaporated, dimethylformamide (40 mL) is added followed by hexyl iodide (35.0 mmol). After 2 days the solvent is removed and the residue is partitioned between ethyl acetate and pH=4 buffer. The organic layer is separated, dried over $MgSO_4$ and evaporated to 8.6 g of a brown solid. Recrystallization from ethanol/water affords 6.23 g (62%) of white crystals, m.p. 65°-67° C.

Analysis for: $C_{17}H_{23}NO_3$ Calculated: C, 70.56; H, 8.01; N, 4.84. Found: C, 70.52; H, 7.98; N, 4.83.

B. 1-[(4-Chlorophenyl)methyl]-5-(hexyloxy)-2-methyl-1H-indole-3-acetic acid

The acid from part A is converted to the methyl ester (m.p. 148°-150° C.) via diazomethane (see Example 16B). To a solution of the ester (4.5 g, 14.83 mmol) in dimethylformamide (40 mL) is added sodium hydride (1.42 g, 29.6 mmol). After 30 minutes 4-chlorobenzyl chloride (2.38 g, 14.83 mmol) is added. After stirring overnight, the solvent is removed and the residue is partitioned between ethyl acetate and pH=4 buffer. The organic layer is separated, dried over $MgSO_4$ and evaporated to a red solid. Sequential recrystallization from ether and isopropanol gives 2.2 g of crystals (36%), m.p. 148°-150° C.

Analysis for: $C_{24}H_{28}ClNO_3$ Calculated: C, 69.64; H, 6.82; N, 3.38. Found: C, 70.00; H, 6.71; N, 3.46.

EXAMPLE 20

2-Methyl-5-(2-quinolinylmethoxy)-1-(2-quinolinylmethyl)-1H-indole-3-carboxylic acid ethyl ester Under an atmosphere of nitrogen, a mixture of ethyl-5-hydroxy-2-methyl-3-indolyl carboxylate (3.5 g, 16 mmol), finely powdered anhydrous potassium carbonate (2.2 g, 16 mmol) and 18-crown-6 (0.48 g, 1.8 mmol) in dry acetonitrile (50 mL) is stirred at room temperature for 0.5 hours. In one portion 2-chloromethylquinoline (free base, 2.85 g, 16 mmol) is added and the mixture is stirred at 55° C. overnight. The reaction (found to be complete by TLC analysis) is filtered hot.

The filtrate affords the desired product (0.75 g, 9%) as a tan solid, m.p. 162°–163° C. Recrystallization from ethyl acetate gives pure product (0.42 g, m.p. 162°–163° C.).

Analysis for: $C_{32}H_{27}N_3O_3$ Calculated: C, 76.63; H, 5.43; N, 8.3. Found: C, 76.20; H, 5.59; N, 8.11.

EXAMPLE 21

α-Methyl-6-(2-quinolinylmethoxy)-9-(2-quinolinylmethyl)-9H-carbazole-2-acetic acid A. 4-Benzyloxyphenylhydrazine hydrochloride A solution of sodium nitrite (3.8 g, 0.055 mol in 20 mL of $H_2O$), is added dropwise to an ice cold stirring suspension of 4-benzyloxyaniline (13.0 g, 0.055 mol in 150 mL of concentrated HCl). The reaction mixture is stirred for 90 minutes at −8° to 10° C. A solution of $SnCl_2.2H_2O$ (32.0 g, 0142 mol in 50 mL concentrated HCl) is added and stirred for 1 hour at 0° C. The reaction mixture is removed from the ice bath and is stirred at room temperature for 20 hours. The mixture is then filtered and washed with water to give 13.0 g (95% yield) of product, m.p. 182°–185° C.

B. 6-Benzyloxy-α-methyl-1,2,3,4-tetrahydrocarbazole-2-acetic acid ethyl ester

A mixture containing 4-benzyloxyphenylhydrazine hydrochloride (37.0 g, 0.148 mol), α-methyl-3-oxocyclohexane acetic acid (40.0 g, 0.235 mol), glacial acetic acid (650 mL) and $H_2O$ (100 mL) is stirred at room temperature under a nitrogen atmosphere for 2.5 hours. The mixture is then refluxed for 20 minutes, cooled and poured into 200 mL of ice/$H_2O$. The precipitate is filtered to give 80 g of red colored crude product.

The crude product is dissolved in ether (600 mL) concentrated $H_2SO_4$ (5 mL) is added and the mixture refluxed for 24 hours. The reaction mixture is cooled, concentrated and diluted with ether (100 mL), then washed with 1N NaOH (2×200 mL), water (2×200 mL) and finally once with brine (200 mL), dried over anhydrous $MgSO_4$, filtered and concentrated to give 40.0 g crude product as a thick oil.

C. 6-Benzyloxy-α-methyl carbazole-2-acetic acid ethyl ester

A mixture consisting of 6-benzyloxy-α-methyl-1,2,3,4-tetrahydrocarbazole-2-acetic acid ethyl ester (15.0 g, 0.0398 mol) xylene (500 mL), and chloranil (10.0 g, 0.0408 mol) is refluxed in the dark under a nitrogen atmosphere for 24 hours. The reaction mixture is concentrated to 200 mL and the precipitate is removed by filtration. The precipitate is triturated with benzene (3×100 mL), the solvent fractions are combined and washed with 1N NaOH (3×150 mL), washed with water until neutral to pH paper, dried over $MgSO_4$, filtered and concentrated to give 15.8 crude product. The crude product is flash chromatographed on silica gel using 15% ethyl acetate/hexane as an eluent to give 7.5 g product as a thick oil.

D. 6-Hydroxy-α-methyl carbazole-2-acetic acid ethyl ester

A mixture consisting of 6-benzyloxy-α-methyl carbazole-2-acetic acid ethyl ester (7.3 g, 0.0195 mol) and ethanol (130 mL) is subjected to hydrogenation over 10% Pd/c (0.9 g) for 18 hours at 35 psi. The reaction mixture is filtered and concentrated to give 5.0 g product as a foam.

E. 6-Hydroxy-α-methyl carbazole-2-acetic acid

A mixture consisting of 6-hydroxy-α-methyl carbazole-2-acetic acid ethyl ester (5.0 g, 0.021 mol), potassium hydroxide (5.0 g, 0.089 mol), methanol (300 mL), and water (20 mL) is refluxed for 15 hours. The reaction mixture is cooled concentrated and acidified with a 1:1 solution of concentrated HCl and water to pH 1. The aqueous layer is extracted with ether (4×300 mL), washed with water (200 mL), brine (200 mL), dried over $MgSO_4$, filtered and concentrated to give 2.6 g of product as a foam.

F. α-Methyl-6-(2-quinolinylmethoxy)-9-(2-quinolinylmethyl)-9H-carbazole-2-acetic acid A mixture consisting of 6-hydroxy-α-methyl carbazole-2-acetic acid (2.6 g, 0.010 mol), dimethyl sulfoxide (200 mL), sodium hydroxide (2.0 g in 20 mL $H_2O$, 0.05 mol) and 2-chloromethylquinoline.HCl (4.0 g, 0.018 mol) is heated to 80° C. for 3 hours. The reaction mixture is cooled, poured into water (1000 mL), and the pH is adjusted to 4 with 1N HCl. The aqueous solution is extracted with ethyl acetate (4×300 mL) and the organic layers are combined, washed with water (2×300 mL), once with brine (300 mL), dried over $MgSO_4$, filtered and concentrated to give 3.0 g of crude product. The latter is chromatographed on silica gel using 10% methanol/methylene chloride as an eluent to give 8 g of product, m.p. 197°–199° C.

Analysis for: $C_{35}H_{27}N_3O_3$ Calculated: C, 78.19; H, 5.06; N, 7.82. Found: C, 76.01; H, 5.02; N, 7.36.

EXAMPLE 22

1-[(4-Chlorophenyl)methyl]-2-methyl-N-(methyl)-N-(hydroxy)-5-(2-quinolinylmethoxy)-1H-indole-3-acetamide three quarters hydrate To a solution of the acid of Example 16 (0.2 g, 0.42 mmol), N-methyl hydroxylamine hydrochloride (0.035 g, 0.42 mmol) and benzotriazole-1-yloxytris(dimethylamino)phosphonium hexafluorophosphate (0.188 g, 0.42 mmol) in methylene chloride (5 mL) is added triethylamine (0.12 mL, 2 equiv). The reaction mixture is stirred overnight and then is quenched by addition of brine. After sequential washes with water, 0.5N HCl and water, the organic layer is dried over $MgSO_4$ and evaporated to afford a crude solid, which upon chloroform recrystallization(twice) affords a crystalline solid, m.p. 192°–194° C. This material is washed sequentially with 0.5N NaOH and water and dried to afford white crystals, m.p. 191°–193° C.

Analysis for: $C_{29}H_{26}ClN_3O_3.\frac{3}{4}H_2O$ Calculated: C, 67.83; H, 5.39; N, 8.18. Found: C, 67.87; H, 5.10; N, 8.39.

EXAMPLE 23

1-[(4-Chlorophenyl)methyl]-2-methyl-N-(phenylsulfonyl)-5-(2-quinolinylmethoxy)-1H-indole-3-acetamide To a solution of the acid of Example 16 (1.0 g, 2.12 mmol), benzene sulfonamide (0.34 g, 2.12 mmol) and benzotriazole-1-yloxytris(dimethylamino)phosphonium hexafluorophosphate (0.94 g, 2.12 mmol) in methylene chloride (25 mL) is added triethylamine (0.6 mL, 2 equiv). The reaction mixture is stirred overnight and then is quenched by addition of brine. After sequential washes with water, 0.5N HCl and water, the organic layer is dried over MgSO$_4$ and evaporated to afford a crude solid, which upon toluene recrystallization affords a crystalline solid, m.p. 194°–197° C.

Analysis for: C$_{34}$H$_{28}$ClN$_3$O$_4$S Calculated: C, 66.93; H, 4.63; N, 6.89. Found: C, 67.01; H, 4.66; N, 7.33.

EXAMPLE 24

1-[(4-Fluorophenyl)methyl]-2-methyl-5-(2-quinolinylmethoxy)-1H-indole-3-acetic acid hemihydrate The title compound is prepared according to the method of Example 16 using 4-fluorobenzyl bromide. A crystalline solid is obtained, m.p. 199°–202° C.

Analysis for: C$_{28}$H$_{23}$FN$_2$O$_3$.½H$_2$O Calculated: C, 72.55; H, 5.21; N, 6.04. Found: C, 72.84; H, 5.31; N, 5.68.

EXAMPLE 25

1-[(4-Bromophenyl)methyl]-2-methyl-5-(2-quinolinylmethoxy)-1H-indole-3-acetic acid hemihydrate The title compound is prepared according to the method of Example 16 using 4-bromobenzyl bromide. A crystalline solid is obtained, m.p. 215°–217° C.

Analysis for: C$_{28}$H$_{23}$BrN$_2$O$_3$.½H$_2$O Calculated: C, 64.12; H, 4.61; N, 5.34. Found: C, 64.40; H, 4.76; N, 5.01.

EXAMPLE 26

1-[(Phenyl)methyl-2-methyl]-5-(2-quinolinylmethoxy)-1H-indole-3-acetic acid tenth hydrate The title compound is prepared according to the method of Example 16 using benzyl bromide. A crystalline solid is obtained, m.p. 199°–202° C.

Analysis for: C$_{28}$H$_{24}$N$_2$O$_3$.0.1H$_2$O Calculated: C, 76.72; H, 5.56; N, 6.39. Found: C, 76.30; H, 5.37; N, 6.34.

EXAMPLE 27

1-[(4-Carboxyphenyl)methyl]-2-methyl-5-(2-quinolinylmethoxy)-1H-indole-3-acetic acid The title compound is prepared according to the method of Example 16 using 4-(chloromethyl)benzoic acid. A crystalline solid is obtained, m.p. 232°–234° C.

Analysis for: C$_{29}$H$_{24}$N$_2$O$_5$ Calculated: C, 72.49; H, 5.03; N, 5.83. Found: C, 72.44; H, 5.18; N, 5.98.

EXAMPLE 28

2-Methyl-5-(2-quinolinylmethoxy)-1-[[4-(2-quinolinylmethoxy)phenyl]methyl]-1H-indole-3-acetic acid hemihydrate The title compound is prepared according to the method of Example 16 using 4-(2-quinolinylmethoxy)benzyl chloride. A crystalline solid is obtained, m.p. 182°–185° C.

Analysis for: C$_{38}$H$_{31}$N$_3$O$_4$.½H$_2$O Calculated: C, 75.73; H, 5.35; N, 6.97. Found: C, 75.41; H, 5.33; N, 6.78.

EXAMPLE 29

2-Methyl-1-pentyl-5-(2-quinolinylmethoxy)-1H-indole-3-acetic acid hemihydrate

The title compound is prepared according to the method of Example 16 using pentyl iodide. A crystalline solid is obtained, m.p. 90°–93° C.

Analysis for: C$_{26}$H$_{28}$N$_2$O$_3$.½H$_2$O Calculated: C, 73.38; H, 6.86; N, 6.58. Found: C, 73.37; H, 7.11; N, 6.41.

EXAMPLE 30

1-Hexyl-2-methyl-5-(2-quinolinylmethoxy)-1H-indole-3-acetic acid three quarters hydrate The title compound is prepared according to the method of Example 16 using hexyl iodide. A crystalline solid is obtained, m.p. 122°–124° C.

Analysis for: C$_{27}$H$_{30}$N$_2$O$_3$.¾H$_2$O Calculated: C, 73.03; H, 7.15; N, 6.30. Found: C, 73.25; H, 7.10; N, 6.30.

EXAMPLE 31

1-Heptyl-2-methyl-5-(2-quinolinylmethoxy)-1H-indole-3-acetic acid

The title compound is prepared according to the method of Example 16 using heptyl iodide. A crystalline solid is obtained, m.p. 127°–131° C.

Analysis for: C$_{28}$H$_{32}$N$_2$O$_3$ Calculated: C, 75.65; H, 7.26; N, 6.30. Found: C, 75.80; H, 7.19; N, 6.26.

EXAMPLE 32

1-Methyl-2-methyl-5-(2-quinolinylmethoxy)-1H-indole-3-acetic acid

The title compound is prepared according to the method of Example 16 using methyl iodide. A crystalline solid is obtained, m.p. 186°–188° C.

Analysis for: C$_{22}$H$_{20}$N$_2$O$_3$ Calculated: C, 73.32; H, 5.59; N, 7.77. Found: C, 73.03; H, 5.69; N, 7.57.

EXAMPLE 33

1-[(4-Chlorophenyl)methyl]-5-(2-quinolinylmethoxy)-1H-indole-3-acetic acid

The title compound is prepared according to the method of Example 16 using 5-hydroxy-1H-indole-3-acetic acid. The desired product is obtained as white crystals, m.p. 158°–159° C.

Analysis for: C$_{27}$H$_{21}$ClN$_2$O$_3$ Calculated: C, 70.97; H, 4.63; N, 6.13. Found: C, 71.13; H, 4.67; N, 6.03.

EXAMPLE 34

1-[(4-Chlorophenyl)methyl]-2-methyl-5-(2-naphthalenylmethoxy)-1H-indole-3-acetic acid The title compound is prepared according to the method of Example 16 using 2-(bromomethyl)naphthalene. A crystalline solid is obtained, m.p. 168°–170° C.

Analysis for: C$_{29}$H$_{24}$ClNO$_3$ Calculated: C, 74.12; H, 5.15; N, 2.98. Found: C, 74.43; H, 5.31; N, 2.74.

EXAMPLE 35

1-[(4-Chlorophenyl)methyl]-2-methyl-5-(phenylmethoxy)-1H-indole-3-acetic acid

The title compound is prepared according to the method of Example 16 using benzyl chloride. A crystalline solid is obtained, m.p. 140°–142° C.

Analysis for: C$_{25}$H$_{22}$ClNO$_3$ Calculated: C, 71.51; H, 5.28; N, 3.34. Found: C, 71.54; H, 5.29; N, 3.47.

EXAMPLE 36

1-[(4-Chlorophenyl)methyl]-2-methyl-5-(2-pyridinylmethoxy)-1H-indole-3-acetic acid The title compound is prepared according to the method of Example 16 using 2-(chloromethyl)pyridine. A crystalline solid is obtained, m.p. 231°–233° C.

Analysis for: $C_{24}H_{21}ClN_2O_3$ Calculated: C, 68.49; H, 5.03; N, 6.66. Found: C, 68.61; H, 5.12; N, 6.39.

EXAMPLE 37

1-[(4-Chlorophenyl)methyl]-2-methyl-5-(2-benzothiazolylmethoxy)-1H-indole-3-acetic acid A. 2-Methyl-5-(2-benzothiazolylmethoxy)-1H-indole-3-acetic acid ethyl ester To a mixture of 5-hydroxy-2-methyl-1H-indole-3-acetic acid ethyl ester (5.6 g, 17.15 mmol) and cesium carbonate (15.0 g, 46.04 mmol) in dimethylsulfoxide (70 mL) that has been previously stirred for 30 minutes is added 2-(chloromethyl)benzothiazole (4.6 g, 25.08 mmol). After 1 hour the reaction is poured into ice water and extracted with ethyl acetate. The organic layer is washed sequentially with 0.1N NaOH, water and brine, dried over $MgSO_4$ and evaporated to a black oil which is purified by flash chromatography (eluant: ethyl acetate-hexane) to afford 5.4 g (59%) of the alkylated ester.

B. 1-[(4-Chlorophenyl)methyl]-2-methyl-5-(2-benzothiazolylmethoxy)-1H-indole-3-acetic acid The title compound is prepared according to the method of Example 16 using 2-methyl-5-(2-benzothiazolylmethoxy)-1H-indole-3-acetic acid ethyl ester and 4-chlorobenzyl chloride; however, the hydrolysis is carried out in aqueous methanol. Recrystallization from acetonitrile affords white crystals, m.p. 175°-176° C.

Analysis for: $C_{26}H_{21}ClN_2O_3S$ Calculated: C, 65.47; H, 4.44; N, 5.87. Found: C, 65.17; H, 4.61; N, 5.81.

EXAMPLE 38

1-[(4-Chlorophenyl)methyl]-2-methyl-5-[(2-phenyl-4-thiazolyl)methoxy]-1H-indole-3-acetic acid The title compound is prepared according to the method of Example 37 using 4-(chloromethyl)-2-phenylthiazole. White crystals are obtained, m.p. 150°-151° C.

Analysis for: $C_{28}H_{23}ClN_2O_3S$ Calculated: C, 66.86; H, 4.61; N, 5.57. Found: C, 66.46; H, 4.59; N, 5.59.

EXAMPLE 39

1-[(4-Chlorophenyl)methyl]-2-methyl-5-[[2-(4-trifluoromethylphenyl)-4-thiazolyl]methoxy]-1H-indole-3-acetic acid The title compound is prepared according to the method of Example 37 using 4-chloromethyl-[(4-trifluoromethyl)-2-phenyl]thiazole. White crystals are obtained, m.p. 196°-197° C.

Analysis for: $C_{29}H_{22}ClF_3N_2O_3S$ Calculated: C, 61.00; H, 3.88; N, 4.91. Found: C, 60.95; H, 3.97; N, 4.89.

EXAMPLE 40

1-[(Phenyl)methyl]-2-methyl-5-[(2-phenyl-4-thiazolyl)methoxy]-1H-indole-3-acetic acid The title compound is prepared according to the method of Example 37 using 4-(chloromethyl)-2-phenylthiazole and benzyl chloride. White crystals are obtained from toluene, m.p. 150°-151° C.

Analysis for: $C_{28}H_{24}N_2O_3S$ Calculated: C, 71.77; H, 5.16; N, 5.98. Found: C, 71.53; H, 5.11; N, 5.90.

EXAMPLE 41

2-Methyl-5-(2-quinolinylmethoxy)-1-[[4-(2-quinolinylmethoxy)phenyl]methylene]-1H-indene-3-acetic acid A. 2-Methyl-5-(2-quinolinylmethoxy)-1H-indene-3-acetic acid methyl ester A mixture of 2-methyl-5-hydroxy-1H-indene-3-acetic acid methyl ester (1.8 g, 8.25 mmol), powdered anhydrous potassium carbonate (1.13 g, 8.25 mmol) and 18-crown-6 (0.219 g) in acetonitrile (21 mL) is stirred at room temperature for 15 minutes. 2-(Chloromethyl)quinoline (1.6 g, 9.08 mmol) is then added and the mixture is stirred for 15 hours at 65° C. After the solvent is removed, the residue is partitioned between water and ethyl acetate. The organic phase is dried over $MgSO_4$ and evaporated. The crude product is purified by flash chromatography (eluant: methylene chloride-ethyl acetate) to afford 2.35 g (79%) of the desired product.

B. 2-Methyl-5-(2-quinolinylmethoxy)-1-[[4-(2-quinolinylmethoxy)phenyl]methylene]-1H-indene-3-acetic acid To a solution of the above ester (1.77 g, 4.93 mmol) in anhydrous methanol (20 mL) is added 4-[(2-quinolinyl)-methoxy]benzaldehyde (1.63 g., 6.19 mmol) followed by dropwise addition of 25% methanolic sodium methoxide (3.46 mL). After the reaction mixture is refluxed for 13 hours, the solvent is removed and water is added. The pH is adjusted to 6.5 and the resulting precipitate is extracted sequentially with methylene chloride and ethyl acetate. The combined extracts are dried over $MgSO_4$ and evaporated to a crude solid which is triturated with diethyl ether and then redissolved in hot ethyl acetate. After the insolubles are filtered off, the solution is concentrated until precipitation occurs. The precipitate is filtered, washed diethyl ether and hexane and dried to afford 1.31 g (45%) of the desired product as a Z/E mixture (7.6/1), m.p. 191°-193° C. (dec.).

Analysis for: $C_{39}H_{30}N_2O_4$ Calculated: C, 79.30; H, 5.12; N, 4.74. Found: C, 79.11; H, 5.05; N, 4.59.

EXAMPLE 42

N-[[1-[(4-Chlorophenyl)methyl]-2-methyl-5-(2-quinolinylmethoxy)-1H-indol-3-yl]methyl]-N'-hydroxyurea To a solution of the acid of Example 16 (0.72 g, 1.52 mmol), in benzene (25 mL) is added triethylamine (0.23 mL, 1.1 equiv) followed by diphenylphosphoryl azide (0.46 g, 1.1 equiv). After the reaction mixture is heated at 90° C. for 1 hour, a solution of hydroxylamine hydrochloride (0.23 g, 2.2 equiv.) in a mixture of triethylamine (0.46 mL) and water (0.25 mL) is added to it, and the reaction mixture is heated at 90° C. overnight. The reaction is quenched by addition of ammonium chloride solution, and the resulting precipitate is filtered off, washed with water and ethyl acetate and dried to afford 0.45 g (59%) of a white solid, m.p. 184°-186° C.

Analysis for: $C_{28}H_{25}ClN_4O_3$ Calculated: C, 67.13; H, 5.03; N, 11.18. Found: C, 66.85; H, 5.06; N, 10.85.

EXAMPLE 43

1-[(4-Chlorophenyl)methyl]-2-methyl-5-(2-quinolinylmethoxy)-1H-indole-acetic acid, tromethamine salt hemi-ethanolate To a hot solution of the acid of Example 16 (0.3 g, 0.64 mmol) in ethanol (20 mL) is added a solution of tromethamine (77 mg, 0.64 mmol) in water (1 mL).

After the reaction mixture is stirred for 2 hours, the solvent is concentrated to half volume and refrigerated overnight. The resulting solid is removed and dried affording 0.21 g of white crystals which decompose at 105° C.

Analysis for: $C_{28}H_{23}ClN_2O_3.C_5H_{11}NO_3.0.5C_2H_6O$ Calculated: C, 64.39; H, 6.01; N, 6.82. Found: C, 64.02; H, 5.82; N, 6.79.

EXAMPLE 44

5-Fluoro-N-hydroxy-N,2-dimethyl-1-[[4-(2-quinolinyl-methoxy)phenyl]methylene]1H-indene-3-acetamide hydrochloride To a chilled mixture of the acid of Example 4 (1.2 g, 2.65 mmol) and dimethylformamide (0.2 mL, 2.68 mmol) in methylene chloride (20 mL) is added oxalyl chloride (0.52 mL, 2.25 equiv). After the reaction mixture is stirred for 1 hour, a solution of N-methylhydroxylamine hydrochloride (0.89 g, 10.63 mmol) in a mixture of triethylamine (1.92 mL), tetrahydrofuran (10 mL) and water (0.25 mL) is added to it, and the reaction mixture is stirred at room temperature overnight. The reaction is poured into 2N HCl and a solid forms (HCl salt). The solid is removed and recrystallized from ethanol affording 0.27 g (19%) of a yellow solid which decomposes at 120° C.

Analysis for: $C_{30}H_{25}FN_2O_3.HCl$ Calculated: C, 69.70; H, 5.07; N, 5.42. Found: C, 70.61; H, 5.10; N, 5.37.

EXAMPLE 45

The compounds 5- and 12-hydroxyeicosatetraenoic acid (5-HETE and 12-HETE) and LTB$_4$ are early arachidonic acid oxidation products in the li cascade, which have been shown to mediate several aspects of inflammatory and allergic response. This is especially true with respect to 5,12-diHETE, which is also denoted as LTB$_4$ [see Ford-Hitchinson, *J. Roy. Soc. Med.*, 74, 831 (1981)]. Compounds which inhibit the PLA$_2$-mediated release of arachidonic acid thereby effectively prevent the oxidation of arachidonic acid to the various leukotriene products via the lipoxygenase cascade. Accordingly, the specificity of action of PLA$_2$ inhibitors can be determined by the activity of test compounds in this assay, which measures the ability of compounds to inhibit the synthesis of LTB$_4$ by rat glycogen-elicited polymorphonuclear leukocytes (PMN) in the presence of exogenous substrate.

The assay is carried out as follows:

Rat polymorphonuclear leukocytes (PMNs) are obtained from female Wistar rats (150-200 g) which receive an injection of 6% glycogen (10 ml i.p.). Rats are sacrificed 18-24 hours post injection by $CO_2$ asphyxiation and the elicited cells are harvested by peritoneal lavage using physiological saline (0.9% NaCl). The exudate is centrifuged at 400×g for 10 minutes. The supernatant fluid is discarded and the cell pellet is resuspended to a concentration of $2.0 \times 10^7$ cells/mL in HBSS containing $Ca^{++}$ and $Mg^{++}$ and 10 $\mu$M L-cysteine.

To 1 mL aliquots of cell suspension, test drugs or vehicle are added, then preincubated at 37° C. for 10 minutes. A23187 (1 $\mu$M), [$^3$H]-AA (3.0 $\mu$Ci/mL) and unlabeled AA (1 $\mu$M) are then added and the samples are further incubated for 10 minutes. The reaction is terminated by centrifugation and pelleting cells. Supernatants are then analyzed by HPLC analysis on a 15 cm×4.6 mm ID supelcosil LC-18 (Supelco)(3M) column, using a two solvent system at a flow rate of 1.4 mL total flow as follows:

| | | |
|---|---|---|
| Solvent A: 70:30 17.4 mM $H_3PO_4$:$CH_3CN$ | | |
| Solvent B. $CH_3CN$ | | |
| Gradient: (system is equilibrated with Solvent A) | | |
| Time | Percent A | Percent B |
| 0 | 100 | 0 |
| 15.0 | 100 | 0 |
| 20.0 | 65 | 35 |
| 40.0 | 65 | 35 |
| 42.0 | 10 | 90 |
| 50.0 | 10 | 90 |
| 50.1 | 100 | 0 |

Percent solvent changes are accomplished in a linear fashion.

Injections: 140 $\mu$L of each supernatant is injected directly onto column and $^3$H arachidonic acid metabolites are monitored using an on-line radioactivity detector (Ramona, IN/US, Fairfield, N.J.).

Standards: $10^4$–$2.0 \times 10^4$ dpm of eicosanoids of interest are injected in 90 $\mu$L EtOH cocktail.

Co-chromatography with standard [$^3$H] leukotriene B$_4$ (LTB$_4$) in medium of stimulated PMN exposed to drug is compared to that found in medium of stimulated cells exposed to no drug, generating percent inhibition.

Results are expressed as percent inhibition at a given compound dose or as an IC$_{50}$ value.

Testing compounds of the invention in this assay gave the following result:

TABLE I

| Compound of Example No. | % Inhibition |
|---|---|
| carprofen | −10* (at 10 $\mu$M) |
| etodolac | 21 (at 0.5 $\mu$M) |
| indomethacin | 31 (at 10 $\mu$M) |
| sulindac | −10* (at 10 $\mu$M) |
| 1 | 96 (at 10 $\mu$M) |
| 2 | 96 (at 10 $\mu$M) |
| 4 | 92 (at 0.5 $\mu$M) |
| 8 | 91 (at 10 $\mu$M) |
| 9 | 96 (at 10 $\mu$M) |
| 10 | 91 (at 10 $\mu$M) |
| 11 | 95 (at 10 $\mu$M) |
| 14 | 91 (at 10 $\mu$M) |
| 16 | 96 (at 10 $\mu$M) |
| 16C | 88 (at 0.5 $\mu$M) |
| 17 | 46 (at 0.5 $\mu$M) |
| 17A | 96 (at 10 $\mu$M) |
| 18 | 88 (at 0.5 $\mu$M) |
| 20 | 92 (at 10 $\mu$M) |
| 21 | 92 (at 10 $\mu$M) |
| 24 | 97 (at 10 $\mu$M) |
| 25 | 93 (at 10 $\mu$M) |
| 26 | 85 (at 10 $\mu$M) |
| 29 | 88 (at 10 $\mu$M) |
| 30 | 90 (at 10 $\mu$M) |
| 31 | 85 (at 10 $\mu$M) |
| 41 | 100 (at 10 $\mu$M) |

*negative number denotes potentiation

EXAMPLE 46

The procedure of Example 45 is also employed for the determination of the extent to which compounds of the invention inhibit the synthesis of the arachidonic acid cyclooxygenase oxidation product PGE$_2$.

In this assay, the procedure of Example 45 is carried out as described. However, in order to determine cyclooxygenase activity, the samples are co-chromatographed with authentic reference [$^3$H]-PGE$_2$.

The results are calculated as in Example 45 and presented below:

TABLE II

| Compound of Example No. | % Inhibition |
|---|---|
| carprofen | 83 (at 10 μM) |
| etodolac | 100 (at 0.5 μM) |
| indomethacin | 100 (at 10 μM) |
| sulindac | 23 (at 10 μM) |
| 1 | 81 (at 10 μM) |
| 2 | 92 (at 10 μM) |
| 4 | 7 (at 0.5 μM) |
| 8 | 47 (at 10 μM) |
| 9 | 75 (at 10 μM) |
| 10 | −41* (at 10 μM) |
| 11 | 80 (at 10 μM) |
| 14 | −48* (at 10 μM) |
| 16 | * (at 10 μM) |
| 16C | * (at 10 μM) |
| 17 | 60 (at 0.5 μM) |
| 17A | 50 (at 10 μM) |
| 18 | −31* (at 0.5 μM) |
| 20 | * (at 10 μM) |
| 21 | −94* (at 10 μM) |
| 24 | −126* (at 10 μM) |
| 25 | −67* (at 10 μM) |
| 26 | −125* (at 10 μM) |
| 29 | −123* (at 10 μM) |
| 30 | −130* (at 10 μM) |
| 31 | −145* (at 10 μM) |
| 41 | −21* (at 0.5 μM) |

*Denotes a potentiation of cyclooxygenase (PGE$_2$ synthesis).

EXAMPLE 47

The compounds of the invention are tested in an in vitro isolated phospholipase A$_2$ assay to determine the ability of the test compounds to inhibit the release of arachidonic acid from an arachidonic acid-containing substrate by the action of phospholipase A$_2$ enzyme from human and non-human sources.

This assay is carried out as follows:

Into a 15 mL polypropylene tube are added the following:

| Agent | Volume, μL | Final Conc. |
|---|---|---|
| $^3$H-AA E. coli substrate [1] | 25 | 5 nmoles PL |
| CaCl$_2$ (0.1M) [2] | 5 | 5 mM |
| Tris-HCl (0.5M) pH 7.5 [3] | 20 | 100 mM |
| Water [4] | 25 | |
| Drug/vehicle [5] | 1 | 50 μM |
| PLA$_2$ | 25 | Volume yielding 12% hydrolysis in 10 min. |
| | 100 | |

*pre-incubate at room temperature 30 min prior to substrate addition.
[1] Prepared by adding 2 mL deionized and distilled water to 2 mL $^3$H-arachidonate labeled E. coli (lower count), to which is added 1 mL of $^3$H-arachidonate labeled E. coli (higher count) to yield a total of 5 m substrate (containing 1000 nmoles phospholipid).
[2] Stock 0.1 m CaCl$_2$, required for enzyme activity.
[3] Stock 0.5 m Trisma-Base. Stock 0.5M Trisma-HCl. Adjust pH to 7.5 (optimum for enzyme).
[4] Deionized and distilled water.
[5] Stock 10 mM prepared in dimethyl sulfoxide. Make 1:2 dilution with dimethyl sulfoxide and add 1 μL to 100 μL assay tube.
[6] Two human PLA$_2$ enzymes are used: a) Semi-purified human platelet acid extract PLA$_2$ (in 10 mM sodium acetate buffer, pH 4.5). Remove protein precipitate by centrifugation at about 2200 rpm for 10 minutes. b) Purified human synovial fluid.

Incubate the 100 μL reaction mixture for 10 minutes at 37° C. in a shaking water bath. The reaction is terminated by the addition of 2 mL tetrahydrofuran, followed by vortexing. NH$_2$ columns (100 μg/mL—Analytichem International) are conditioned with 0.5 mL tetrahydrofuran followed by 0.5 mL tetrahydrofuran/water (2 mL:0.1 mL, v/v).

The sample is loaded onto the columns and slowly drawn through them. The hydrolyzed arachidonic acid retained in the columns is eluted therefrom with 1 mL tetrahydrofuran/glacial acetic acid (2%). The arachidonic acid is transferred to scintillation vials and quantitated by β-counting analysis. A "total counts" sample is prepared by pipetting 25 μL $^3$H-arachidonate E. coli directly into a scintillation vial to which is added 1 mL tetrahydrofuran: 10 mL aquasol (scintillation cocktail) is added to all samples.

Calculations:

$$\% \text{ hydrolysis} = \frac{[3H]AA \text{ dpm (sample)} - [3H]AA \text{ dpm (nonspecific hydroylsis)}}{\text{total counts dpm}} \times 100$$

$$\% \text{ change} = \frac{\text{vehicle dpm} - \text{drug dpm}}{\text{vehicle dpm}} \times 100$$

Activity of Standard Drugs:

| | IC$_{50}$ (μM) | |
|---|---|---|
| Drug | Human Platelet PLA$_2$ | Human Synovial PLA$_2$ |
| Arachidonic Acid | 8.6 | 3.2 |
| Monoalide | 25.2 | 0.14 |

When tested in this assay, the compounds of the invention gave the following results:

TABLE III

| Compound of Example No. | % Inhibition at 10 μM HP* | % Inhibition at 10 μM HSF** | IC$_{50}$ (μM) HP | IC$_{50}$ (μM) HSF |
|---|---|---|---|---|
| sulindac | 33 | 34 | | 30.2 |
| indomethacin | | 38(at 50 μM) | | 144.8 |
| 1 | | | — | 9.7 |
| 2 | | | | 3.6 |
| 4 | 58 | 48 | | |
| 16 | | 46 | | 4.1 |
| 17 | | 58 | | 14.9 |
| 18 | 47 | 30 | | 27.0 |
| 19 | 71 | 45 | | |
| 23 | | 64 | | |
| 24 | | 56 | | |
| 25 | | 11 | | |
| 26 | | 92 | | 2.6 |
| 27 | | 45 | | |
| 28 | | 41 | | |
| 29 | | 53 | | 15.5 |
| 30 | | 46 | | 16.4 |
| 31 | | 32 | | |
| 32 | | 36 | | |
| 33 | | 38 | | |
| 34 | | | | 33.7 |
| 35 | | 28 | | 52.9 |
| 36 | | 46 | | |
| 37 | | 39 | | |
| 38 | | 31 | | |
| 39 | | 46 | | |
| 40 | | 42 | | |
| 41 | | 90 | | 3.8 |

*human platelet
**human synovial fluid

EXAMPLE 48

The ability of the compounds of the invention to inhibit paw edema induced by the exogenous administration of PLA$_2$ is measured in the in vivo PLA$_2$ murine paw edema assay.

The assay is carried out as follows:

Non-fasted, male CD-1 mice (8 weeks old; 31-36 grams) are placed in plastic boxes in groups of six. The right hind paw volume is measured using mercury plethysmography (zero time). Compounds are dosed orally (0.5 mL of 0.5% Tween-80) 1 or 3 hours prior to $PLA_2$ injection or intravenously (0.2 mL in 0.3% dimethylsulfoxide/saline) 3 minutes prior to $PLA_2$ injection. A solution of purified $PLA_2$, from the diamond back cotton mouth snake (*A. piscivorus piscivorus*) is prepared in saline at a concentration of 6 μg/mL. Fifty (50) μL (0.3 μg) of this $PLA_2$ solution is injected subcutaneously into the right hind paw with a plastic 1 mL plastic syringe (27 gauge, 1" needle). Paw volume of the injected paw is measured again at 10 minutes, 30 minutes and 60 minutes after $PLA_2$ injection. Animals are euthanized with $CO_2$ at the completion of the study.

The paw edema is calculated by subtracting the zero time volume from the volume recorded at each time period. Mean paw edema for each treatment group is then calculated and expressed as (μL+S.E.). Drug effects are expressed as a percent change from control (vehicle) values. Statistical significance is determined by a one-way analysis of variance with LSD comparison to control ($p<0.05$). $ED_{50}$'s are determined using repression analysis.

The activity of standard drugs in this assay is as follows:

| Compound | $ED_{50}$ mg/kg p.o. at +10 min. |
|---|---|
| Cyproheptadine | 3.1 |
| BW755C | 50 |
| Dexamethasone* | 10 |
| Naproxen | 18 |
| Aristolochic Acid** | Not Active |
| Luffarrellolide** | Not Active |

*p.o. - 3 hr.
**Some activity (30% inhibition) only when co-injected with enzyme.

When tested in this assay, the compounds of the invention gave the following results:

TABLE V

| Compound of Example No. | Dose mg/kg | % Change in Edema | | |
|---|---|---|---|---|
| | | 10 min | 30 min | 60 min |
| indomethacin | 10 (p.o.)** | −32 | −31 | −42 |
| 1 | 10 (i.v.)* | −6 | −9 | −40 |
| | 100 (p.o.) | +4 | −27 | −6 |
| 2 | 10 (i.v.) | −39 | −43 | −37 |
| | 100 (p.o.) | −6 | −22 | +18 |
| 18 | 30 (i.p.)*** | | −19 | |
| 19 | 30 (i.p.) | | −30 | |
| | 60 (i.p.) | | −34 | |

*intravenous
**peroral
***intraperitoneal

The results show that the compounds of the invention are effective in vivo in inhibiting edema induced by the exogenous administration of snake venom $PLA_2$.

EXAMPLE 49

The compounds of the invention are evaluated for their ability to inhibit the lipoxygenase and/or cyclooxygenase pathways of arachidonic acid metabolism in the in vivo murine zymosan peritonitis assay.

This assay is carried out as follows:

Male CD-1 mice (8 weeks old) are placed in plastic boxes in groups of six. Animals are injected with 1 mL i.p. of either 1% zymosan in pyrogen free 0.9% saline or saline (unstimulated control). Compounds are dosed orally 1 hour prior to zymosan injection. Twenty minutes after zymosan injection, the mice are asphyxiated by $CO_2$ inhalation and the peritoneal cavity is lavaged with 2 mL ice cold Hanks Balanced Salt Solution (HBSS) without $CaCl_2$, $MgSO_4.7H_2O$ and $MgCl_2.6H_2O$. Peritoneal lavage fluid from each mouse is removed by syringe and placed in 5 mL plastic test tubes put on ice and volume is noted. Preparation of samples for evaluation by ELISA is as follows: Samples are centrifuged at 800×g for 15 minutes; 1 mL of the supernatant is added to 8 mL ice cold methanol and kept at −70° C. overnight to precipitate protein; and samples are then centrifuged at 800×g for 15 minutes, followed by a drying procedure in a Savant speed vac concentrator. The samples are reconstituted with 1 mL ice cold ELISA buffer and stored at −70° C. until assayed. The assay for eicosanoids ($LTC_4$ and 6-keto-$PGF_{1\alpha}$) is performed according to conventional ELISA procedures.

Compounds to be tested orally are suspended in 0.5% Tween 80. Compounds to be tested intraperitoneally are suspended in 0.5% methylcellulose in 0.9% saline.

The total metabolite level in lavage fluid/mouse is calculated and the significance is determined by a one-way analysis of variance with LSD comparisons to control ($p \leq 0.05$). Drug effects are expressed as a percent change from control values.

The activity of standard drugs in this assay is as follows:

| Compound | $ED_{50}$ mg/kg p.o. | |
|---|---|---|
| | $LTC_4$ | 6-keto-$PGF_{1\alpha}/TxB_2$ |
| BW755C | <10 | 22.0 |
| Phenidone | 24.0 | <30.0 |
| Indomethacin | Not Active | 0.126 |
| Ibuprofen | Not Active | 7.0 |

When tested in this assay a compound of the invention and the anti-inflammatory compound etodolac gave the following results:

TABLE VI

| Compound of Example No. | Dose mg/kg | % Inhibition | |
|---|---|---|---|
| | | $LTC_4$ | 6-keto-PGF |
| indomethacin | 10(p.o.)* | +25 | |
| 10 | 50(p.o.) | 11 | −5** |
| 11 | 50(p.o.) | −49** | 47 |

*perorally administered
**negative values denote potentiation

The results show that the compounds of the invention exert an inhibitory effect on both the lipoxygenase pathway and the cyclooxygenase pathway.

EXAMPLE 50

The $LTD_4$ antagonist activity of the compounds of the invention is assessed in the in vitro isolated guinea pig trachea assay.

This assay is carried out as follows:

Male Hartley guinea pigs (350–400 g) are euthanized by a blow to the head, the neck is opened and the trachea removed. The trachea is maintained in aerated physiological salt solution, cleared of connective tissue and fat and cut into rings approximately 2 mm in width (usually containing two cartilaginous segments per ring). Two pieces of silk suture are then passed through the lumen of the tracheal ring and are tied around the cartilage, one on each side of the trachealis muscle. The tracheal ring is suspended between a glass hook and a force displacement transducer in a 10 mL organ bath for measurement of isometric tension. Tissues are maintained at 37° C. in aerated (95% $CO_2$/5% $CO_2$) physiological salt solution of the following composition: NaCl (100 mM), $KH_2PO_4$ (1.18 mM), KCl (4.74 mM), $CaCl_2$ (2.5 mM), $MgSO_4 \cdot 7 H_2O$ (1.19 mM), $NaHCL_3$(25 mM), dextrose (11.1 mM) and indomethacin (1 $\mu$M). The tracheal rings are maintained at 2 g resting tension and equilibrated for 45 minutes (with frequent washing and readjustment of resting tension).

The tracheal rings are first contracted by the addition of carbachol ($3 \times 10^{-6}$M), to determine tissue responsiveness and establish a reference contraction. On attainment of a stable level of contraction (approximately 30 minutes), the tissues are washed several times until baseline tension has been restored and then re-equilibrated for 30 minutes. The tissues are then incubated for 45 minutes with a test antagonist (either $1 \times 10^{-6}$M or $1 \times 10^{-5}$M) or 10 $\mu$L of an appropriate solvent control (control, non-treated). One tissue in each group serves as the control. Twenty minutes prior to the construction of the $LTD_4$ cumulative concentration-response curve, L-cysteine ($1 \times 10^{-2}$M final bath concentration) is added to inhibit bioconversion of $LTD_4$ to $LTE_4$. Only one $LTD_4$ concentration-response curve is constructed in each tissue.

All responses to $LTD_4$ in an individual tissue are measured as a percentage of the reference contraction of that tissue to carbachol. $LTD_4$ antagonist activity is determined by comparison of the concentration response curves of $LTD_4$ in the presence and absence of antagonist. Assessment of the relative rightward shift of the antagonist treated curve relative to the solvent (control) treated tissue is calculated as a concentration ratio (Eq. A) and used in subsequent calculations to derive an antagonist $pK_B$ value (Eqs B and C). In the event that the maximum response to $LTD_4$ is depressed, the $EC_{50}$ for that particular curve is determined, an "apparent" $pK_B$ reported, and the compound reported as "non-competitive."

$$\text{Concentration Ratio (CR)} = \frac{EC_{50} \text{ treated tissue}}{EC_{50} \text{ control}} \quad \text{A)}$$

$$K_B = \frac{[\text{Test Compound}]}{CR - 1} \quad \text{B)}$$

$$-\log K_B = pK_B \quad \text{C)}$$

If a compound is found to be active and/or depress the maximal response to $LTD_4$, then a range of concentrations of the test compound should be used generating multiple concentration ratios which would then be used to perform a Schild analysis, and determination of a $pA_2$ value where appropriate.

The activity of reference leukotriene antagonists in this assay is as follows:

| Compound | $pK_B$ |
| --- | --- |
| Ly-171,883 | 7.44 ± 0.12 |
| Wy-48,252 | 6.90 ± 0.23 |

When tested in this assay, a compound of the invention gave the following results:

TABLE VII

| Compound of Example No. | $pK_B$ | Concentration Ratio (M) |
| --- | --- | --- |
| 9 | 6.26 ± 0.28 | $1 \times 10^{-5}$ |
| 18 | 5.85 ± 0.12 | $1 \times 10^{-5}$ |
| 43 | 6.0 | $1 \times 10^{-5}$ |

The above results demonstrate that the compounds tested have significant leukotriene antagonist activity as measured in the in vitro isolated guinea pig trachea assay.

EXAMPLE 51

The compounds of the invention are further tested in the rat carrageenan paw edema assay to determine their ability to inhibit the acute inflammatory response.

This assay is carried out as follows:

140-180 g Male Sprague-Dawley rats, in groups of 6 animals are injected subcutaneously in the right paw with 0.1 mL of 1% carrageenan at zero time. Mercury plethysmographic readings (mL) of the paw are made at zero time and 3 hours later. Test compounds are suspended or dissolved in 0.5% methylcellulose and given perorally 1 hour prior to carrageenan administration.

The increase in paw volume (edema in mL) produced by the carrageenan is measured. Paw edema is calculated (3 hour volume minus zero time volume), and percent inhibition of edema is determined. Unpaired Student's t-test is used to determine statistical significance.

The activity of standard drugs in this assay is as follows:

| Drug | Oral $ED_{50}$ (95% C.L.) mg/kg |
| --- | --- |
| Indomethacin | 3.7 (0.6, 23.8) |
| Aspirin | 145.4 (33.1, 645.6) |
| Phenylbutazone | 26.2 (2,3, 291.0) |

When tested in this assay, a compound of the invention and the anti-inflammatory drug etodolac gave the following results:

TABLE VIII

| Compound of Example No. | Dose* (mg/kg) | % Inhibition 50 mg/kg (peroral) | Oral $ED_{50}$ mg/kg |
| --- | --- | --- | --- |
| etodolac | | | 23 |
| 10 | 50 | 48 | |
| 11 | 50 | +1 | |
| 14 | 50 | 27 | |

*administered perorally

The results shown that the compounds tested have activity in the rat carrageenan paw edema assay, evidencing an effect on the acute inflammatory response.

EXAMPLE 52

The assay of this Example measures the ability of the compounds tested to inhibit 5-lipoxygenase in human whole blood.

This assay is carried out as follows:

Blood is obtained in 50-100 ml quantities from male donors. White blood cell counts and differentials are made. Two ml of blood are placed in a 15 ml polypropylene test tube. Compounds are solubilized in dimethylsulfoxide and diluted 1:10 in 10% bovine serum albumin in phosphate buffered saline, pH 7.4 resulting in a final dimethylsulfoxide concentration of 0.1% in the blood. Then, compounds are added to the blood in a shaking water bath at 37° C. for 10 minutes prior to the addition of 30 μM calcium ionophore (A23187; Sigma). After ionophore administration, whole blood samples are mixed and incubated for 20 minutes at 37° C. in a shaking water bath. Incubation is terminated by placing samples in an ice bath and immediately adding ethylene glycol-bis-(β-aminoethyl ether)-N,N,N',N'-tetraacetic acid (10 mM). Samples are mixed and centrifuged at 1200× g for 15 minutes at 4° C. Preparation of samples for evaluation by RIA or ELISA is carried out by the following protocol. Plasma is removed from sample tubes, placed in 15 ml polypropylene test tubes containing 8 ml methanol, and then vortexed to precipitate protein. Samples are stored at −70° C. overnight. The next day, samples are centrifuged at 200× g for 15 minutes at 4° C. to pellet the precipitate. Samples are dried in a Savant speed vac concentrator, reconstituted to original volume with ice cold RIA or ELISA buffer, and stored at −70° C. until assayed. The assay for eicosanoids ($LTB_4$, $TxB_2$, and $PGE_2$) is performed as described by the manufacturer of the [$^3$H]-RIA kit or ELISA kit ($LTB_4$-Amersham, $TxB_2$ and $PGE_2$-Caymen Chemical).

The total eicosanoid level in 2 ml of blood is calculated and reported as ng/$10^6$ neutrophils. Significance is determined by a one-way analysis of variance with least significant difference (LSD) comparisons to control ($p \leq 0.05$) and $IC_{50}$'s (μM) are determined by regression analysis (Finney, 1978). Drug effects are expressed as percent change from control values.

Compounds tested in vitro are solubilized in dimethylsulfoxide and diluted 1:10 in 10% bovine serum albumin in phosphate buffer saline resulting in a final dimethylsulfoxide concentration of 0.1% in the blood.

The results for compounds of the invention tested in this assay are presented in Table IX.

TABLE IX

| Compound of Example No. | Dose (μM) | % Inhibition of $LTB_4$ | ($IC_{50}$*) |
|---|---|---|---|
| A-64077 | 25 | 72 | (3.0) |
| L-663,536 | 3 | 96 | |
| 16 | 25 | 18 | |
| 22 | 25 | 78 | (39.8) |
| 42 | 25 | 89 | (5.6) |
| 44 | 25 | 94 | (4.5) |

*μM

EXAMPLE 53

The ability of the compounds of the invention to antagonize $LTD_4$ is assessed in the in vivo antigen-induced guinea pig bronchoconstriction assay.

This assay is carried out as follows:

A. Airway hyperreactivity

Male guinea pigs (Charles River, Wilmington, Mass.) are sensitized 3-4 weeks prior to antigen challenge by administration of 2 i.m. injections of ovalbumin (OA), 1 into each hind limb (35 mg total). Sensitized guinea pigs (500-650 g) are pretreated with pyrilamine (2.5 mg/kg i.p.) 1 hour before aerosol challenge to prevent hypoxic collapse and death, and then challenged while conscious with an aerosol of 0.2% OA (in normal saline), or saline only, for 3 minutes using a Devilbiss model 100 nebulizer (Somerset, Pa.). For pharmacological studies, drugs or vehicle (0.5% Tween 80 in water) are administered p.o. at appropriate times pre- and post-challenge to animals that have been fasted overnight prior to experimentation.

Twenty four hours following aerosol exposure, each guinea pig is anesthetized by urethane (1.2 g/kg i.p.). A carotid artery and jugular vein are cannulated to allow for the monitoring of blood pressure and the administration of drugs, respectively. The trachea is then cannulated and connected to a Harvard Apparatus rodent ventilator (S. Natick, Mass.). Spontaneous respiration is abolished by the administration of succinylcholine (2.5 mg/kg i.v.). The animals are then ventilated with room air at a rate of 65 breaths per minute. Airway inflation pressure is measured using a Statham pressure transducer (Gould Instruments, Cleveland, Ohio) connected to the tracheal cannula via a side-arm and recorded on a Grass Instruments recorder (Quincy, Mass.). The tidal volume (approximately 10 cc/kg) is adjusted to give a baseline inflation pressure of 8-10 cm $H_2O$ at end inspiration. Animals are then allowed 20 minutes to stabilize.

Following the stabilization period, a dose-response curve to bronchoconstriction induced by i.v. methacholine (MCH) or $LTD_4$ is generated in each animal in a non-cumulative fashion. The bronchoconstriction produced by MCH or $LTD_4$ is expressed as the peak increase over baseline in end-inspiratory inflation pressure (in cm $H_2O$), which occurs within 4-5 breaths following the administration of each dose. After the peak effect of each injection of MCH or $LTD_4$ the expiratory tube of the tracheal cannula is occluded for 3 breaths, as hyperinflation of the lungs facilitates the return of airway inflation pressure to the original baseline. The standard doses of MCH used to generate a dose-response curve in each animal are 1, 2, 3, 5 10, 15, 20, 30, 50 and 100 mg/kg, whereas the standard doses of $LTD_4$ used to generate a dose-response curve in each animal are 0.01, 0.1, 0.2, 0.3, 0.5, 0.1, 2.0, and 3.0 μg/kg. A dose-response curve for MCH- or $LTD_4$-induced bronchoconstriction is then generated from each group of animals, with data points on the curves representing the mean values and standard errors for inflation pressures.

In three additional airway hyperreactivity protocols, (1) guinea pigs are challenged with an aerosol of OA or saline once daily for 3 days and MCH or $LTD_4$ dose-response curves are generated 24 hours following the third challenge, (2) MCH dose-response curves are generated 24 hours following a single aerosol challenge with a 10-fold more concentrated (2%) OA solution or with saline and (3) MCH dose-response curves are generated 72 hours following a single aerosol challenge with a standard OA solution or with saline. In all airway hyperreactivity studies OA-challenged and saline-challenged animals are tested in parallel. In the pharmacological studies, in which MCH is the only agonist used, OA-challenged drug-treated animals are tested in parallel with matched OA-challenged vehicle-controls and saline-challenged vehicle-controls. There is an n of 6-8 animals per group.

B. Resistance and compliance measurements

Alterations in isovolumetric airway resistance ($R_L$) and dynamic compliance ($C_{dyn}$) associated with antigen-induced airway hyperreactivity to MCH are determined using 3 saline-challenged guinea pigs and 4 OA-challenged guinea pigs. Anesthetized and ventilated guinea pigs are prepared as described above. In addition, a fluid-filled PE-90 catheter is inserted into the distal esophagus. Transpulmonary airway pressure is measured from a solid-state differential pressure transducer with a 1-70 cm H₂O range (Sensym, Sunnyvale, Calif.), attached to the esophageal catheter and to a side-arm of the tracheal catheter. Air flow is measured from a heated Fleisch 0000 pneumotachograph (Switzerland), calibrated by volume. $C_{dyn}$ and $R_L$ are then calculated on a breath by breath basis by a Ponemah pulmonary data acquisition system (Simsbury, Conn.). In these experiments MCH is given in doses of 3 and 5 mg/kg, which produces the greatest differences in inflation pressure measurements between OA- and saline-challenged groups.

C. Bronchoconstriction (BC) protocols

Guinea pigs are sensitized as described above. Following the 3-4 week sensitization period animals are fasted overnight prior to experimentation. Conscious animals are then dosed p.o. with drug or vehicle alone (0.5% Tween 80 in H₂O) at appropriate times prior to antigen challenge, with 4 doses of each drug tested. Subsequently, animals are anesthetized, cannulated and ventilated as described above. After a 20 minute stabilization period, animals are given i.v. injections of pyrilamine (5 mg/kg), propranolol (0.1 mg/kg) and indomethacin (10 mg/kg) at 15, 10 and 5 minutes, respectively, prior to antigen challenge. This pretreatment results in an LT-dependent bronchoconstriction following antigen challenge, which is accomplished by administration of an OA aerosol (1 mg/mL) for 15 min via a Devilbiss model 25 ultrasonic nebulizer in-line between the animal and ventilator. Only one bronchoconstriction per animal is induced. End-inspiratory inflation pressure (in cm H₂O over baseline) is measured at 5, 10 and 15 minutes post-OA challenge and summed for each drug-treated and matched vehicle-control animal. A mean value and standard error for the % inhibition of control bronchoconstriction in each drug-treated group is then calculated. There is an n of 6-8 per group.

Data from the antigen-induced bronchoconstriction studies are analyzed by using a One-Way Analysis of Variance, followed by Fisher's Least Significant Differences Test. MCH or LTD₄ dose-response curves from each airway hyperreactivity experiment are compared for significant differences by using a Repeated Measures Multiple Analysis of Variance. For a pharmacological experiment to be considered valid, MCH dose-response curves generated in the OA-challenged vehicle-control group and the saline-challenged vehicle-control group have to be significantly different from each other. A drug is then considered to be active if the MCH dose-response curve generated in the OA-challenged drug-treated group is not significantly different from that generated in the saline-challenged vehicle-control group. Conversely, a drug is considered to be inactive if the MCH dose-response curve generated in the OA-challenged drug-treated group is not significantly different from that generated in the OA-challenged vehicle-control group. If the MCH dose-response curve from the OA-challenged drug-treated group is not significantly different from the curves from either of the 2 control groups the results are considered inconclusive. Statistical significance is accepted at the 95% level of confidence (p<0.05).

The test results for a compound of the invention tested in this assay is presented in Table X.

TABLE X

| Compound | % Inhibition of OA-BC (dose, route) |
|---|---|
| Zileuton | 67 (50 mg/kg, po) |

TABLE X-continued

| Compound | % Inhibition of OA-BC (dose, route) |
|---|---|
| MK-886 | 51 (25 mg/kg, po) |
| Example 43 | 67 (50 mg/kg, po) |

What is claimed is:
1. A compound having the formula

$A(CH_2)_nO\text{-}B$ wherein
A is a group having the formula

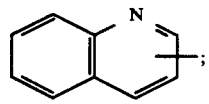

n is 1-2;
B is

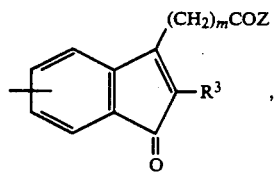

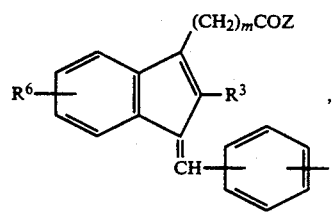

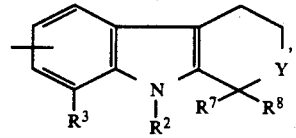

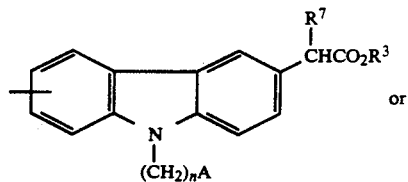 or

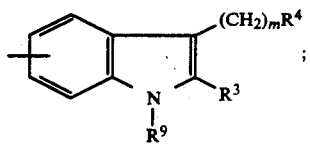

wherein
R² is hydrogen or lower alkyl;
R³ is hydrogen or lower alkyl;
R⁴ is —CO₂R²;
m is 0-3;
R⁵ is phenyl or phenyl substituted by halo, lower alkylthio, lower alkylsulfinyl or lower alkylsulfonyl;

$R^6$ is halo;
$R^7$ is lower alkyl;
Y is —CH$_2$— or —O—;
$R^8$ is lower alkyl or —(CH$_2$)$_m$CO$_2$R$^3$;
$R^9$ is

or —CH$_2$R$^{10}$;

$R^{10}$ is lower alkyl, phenyl or phenyl substituted with carboxy, halo, loweralkylthio or loweralkylsulfonyl;

Z is hydrogen, lower alkyl or —N(CH$_3$)OH;
and the pharmacologically acceptable salts thereof.

2. The compound of claim 1, 3-[(4-chlorophenyl)methylene]-[2-methyl-6-(2-quinolinylmethoxy)]-3H-indene-1-acetic acid.

3. The compound of claim 1, 2-methyl-3-[[4-(methylthio)phenyl]methylene]-6-(2-quinolinylmethoxy)-3H-indene-1-acetic acid.

4. The compound of claim 1, 2-methyl-3-[[(4-methylsulfinyl)phenyl]methylene]-6-(2-quinolylmethoxy)-3H-indene-1-acetic acid.

5. The compound of claim 1, 5-fluoro-2-methyl-1-[[4-(2-quinolinylmethoxy)phenyl]methylene]-1H-indene-3-acetic acid.

6. The compound of claim 1, 3-[(4-chlorophenyl)methylene]-[2-methyl-6-(2-quinolinylmethoxy)]-3H-indene-1-acetic acid methylester.

7. The compound of claim 1, 1,8-diethyl-1,3,4,9-tetrahydro-6-(2-quinolinylmethoxy)pyrano[3,4-b]indole-1-acetic acid.

8. The compound of claim 1, 1-ethyl-1,3,4,9-tetrahydro-6-(quinolinylmethoxy)pyrano[3,4-b]indole-1-acetic acid.

9. The compound of claim 1, 1-methyl-1,3,4,9-tetrahydro-6-(2-quinolinylmethoxy)pyrano[3,4-b]indole-1-acetic acid.

10. The compound of claim 1, 1-ethyl-2,3,4,9-tetrahydro-6-(2-quinolinylmethoxy)-1H-carbazole-1-acetic acid.

11. The compound of claim 1, 1,3,4,9-tetrahydro-1-propyl-6-(2-quinolinylmethoxy)pyrano[3,4-b]indole-1-acetic acid.

12. The compound of claim 1, 1-ethyl-1,3,4,9-tetrahydro-6-(2-quinolinylmethoxy)pyrano[3,4-b]indole-1-acetic acid, methyl ester.

13. The compound of claim 1, 1,3,4,9-tetrahydro-1,1-dimethyl-6-(2-quinolinylmethoxy)pyrano[3,4-b]indole.

14. The compound of claim 1, 1,3,4,9-tetrahydro-1,1-diethyl-6-(2-quinolinylmethoxy)pyrano[3,4-b]indole.

15. The compound of claim 1, 1-[(4-chlorophenyl)methyl]-2-methyl-5-(2-quinolinylmethoxy)-1H-indole-3-acetic acid.

16. The compound of claim 1, 1-[(4-chlorophenyl)methyl]-2-methyl-5-(2-quinolinylmethoxy)-1H-indole-3-acetic acid methyl ester.

17. The compound of claim 1, 1-(4-chlorobenzoyl)-2-methyl-5-(2-quinolinylmethoxy)-1H-indole-3-acetic acid.

18. The compound of claim 1, 1-(4-chlorobenzoyl)-2-methyl-5-(2-quinolinylmethoxy)-1H-indole-3-acetic acid methyl ester.

19. The compound of claim 1, 1-[(4-fluorophenyl)methyl]-2-methyl-5-(2-quinolinylmethoxy)-1H-indole-3-acetic acid.

20. The compound of claim 1, 1-[(4-bromophenyl)methyl]-2-methyl-5-(2-quinolinylmethoxy)-1H-indole-3-acetic acid.

21. The compound of claim 1, 1-[(phenyl)methyl]-2-methyl]-5-(2-quinolinylmethoxy)-1H-indole-3-acetic acid.

22. The compound of claim 1, 1-[(4-carboxyphenyl)methyl]-2-methyl-5-(2-quinolinylmethoxy)-1H-indole-3-acetic acid.

23. The compound of claim 1, 2-methyl-1-pentyl-5-(2-quinolinylmethoxy)-1H-indole-3-acetic acid.

24. The compound of claim 1, 1-hexyl-2-methyl-5-(2-quinolinylmethoxy)-1H-indole-3-acetic acid.

25. The compound of claim 1, 1-heptyl-2-methyl-5-(2-quinolinylmethoxy)-1H-indole-3-acetic acid.

26. The compound of claim 1, 1-methyl-2-methyl-5-(2-quinolinylmethoxy)-1H-indole-3-acetic acid.

27. The compound of claim 1, 1-[(4-chlorophenyl)methyl]-5-(2-quinolinylmethoxy)-1H-indole-3-acetic acid.

28. The compound of claim 1, 1-[(4-chlorophenyl)methyl]-2-methyl-5-(2-quinolinylmethoxy)-1H-indole-acetic acid, tromethamine salt.

29. The compound of claim 1, 5-fluoro-N-hydroxy-N,2-dimethyl-1-[[4-(2-quinolinylmethoxy)phenyl]methylene]-1H-indene-3-acetamide hydrochloride.

* * * * *